United States Patent
Dichterman et al.

(10) Patent No.: US 11,311,204 B2
(45) Date of Patent: Apr. 26, 2022

(54) SYSTEMS AND METHODS FOR RECONSTRUCTION OF INTRABODY ELECTRICAL READINGS TO ANATOMICAL STRUCTURE

(71) Applicant: Navix International Limited, Road Town (VG)

(72) Inventors: Eli Dichterman, Haifa (IL); Yitzhack Schwartz, Haifa (IL); Yizhaq Shmayahu, Ramat-HaSharon (IL); Shlomo Ben-Haim, Milan (IT)

(73) Assignee: Navix International Limited, Road Town (VG)

( * ) Notice: Subject to any disclaimer, the term of this patent is extended or adjusted under 35 U.S.C. 154(b) by 178 days.

(21) Appl. No.: 16/476,875

(22) PCT Filed: Jan. 12, 2018

(86) PCT No.: PCT/IB2018/050192
§ 371 (c)(1),
(2) Date: Jul. 10, 2019

(87) PCT Pub. No.: WO2018/130974
PCT Pub. Date: Jul. 19, 2018

(65) Prior Publication Data
US 2019/0336035 A1  Nov. 7, 2019

Related U.S. Application Data

(60) Provisional application No. 62/546,775, filed on Aug. 17, 2017, provisional application No. 62/445,433, filed on Jan. 12, 2017.

(51) Int. Cl.
*A61B 5/0536* (2021.01)
*A61B 5/0538* (2021.01)
(Continued)

(52) U.S. Cl.
CPC .......... *A61B 5/0536* (2013.01); *A61B 5/0538* (2013.01); *A61B 5/068* (2013.01); *A61B 5/6852* (2013.01)

(58) Field of Classification Search
CPC ..... A61B 5/0536; A61B 5/0538; A61B 5/065; A61B 5/066; A61B 5/068; A61B 5/282;
(Continued)

(56) References Cited

U.S. PATENT DOCUMENTS 5,465,730 A * 11/1995 Zadehkoochak .... A61B 5/0536
600/547
5,553,611 A    9/1996 Budd et al.
(Continued)

FOREIGN PATENT DOCUMENTS

CN    102056537    5/2011
CN    103687533    3/2014
(Continued)

OTHER PUBLICATIONS

International Preliminary Report on Patentability dated Aug. 22, 2019 From the International Bureau of WIPO Re. Application No. PCT/IB2018/050784. (11 Pages).
(Continued)

*Primary Examiner* — Patrick Fernandes
*Assistant Examiner* — Severo Antonio P Lopez

(57) ABSTRACT

In some embodiments, a body cavity shape of a subject is reconstructed based on intrabody measurements of voltages by an intrabody probe (for example, a catheter probe) moving within a plurality of differently-oriented electromagnetic fields crossing the body cavity. In some embodiments, the method uses distances between electrodes as a spatially calibrated ruler. Positions of measurements made with the intrabody probe in different positions are optionally related by using spatial coherence of the measured electro-
(Continued)

magnetic fields as a constraint. Optionally, reconstruction is performed without using a detailed reference (image or simulation) describing the body cavity shape. Optionally, reconstruction uses further information to refine and/or constrain the reconstruction; for example: images, simulations, additional electromagnetic fields, and/or measurements characteristic of body cavity landmarks. Optionally, reconstruction accounts for time-dependent cavity shape changes, for example, phasic changes (e.g., heartbeat and/or respiration), and/or changes in states such as subject hydration, edema, and/or heart rate.

33 Claims, 11 Drawing Sheets

(51) Int. Cl.
*A61B 5/06* (2006.01)
*A61B 5/00* (2006.01)

(58) Field of Classification Search
CPC ....... A61B 5/283; A61B 5/287; A61B 5/6852; A61B 34/20; A61B 2034/2051; A61B 5/062; A61B 5/0035; A61B 90/36; A61B 8/12; A61B 6/466; A61B 8/483; A61B 5/0073; A61B 5/055; A61B 18/1492; G06T 15/00; G06T 19/003; G06T 2200/04

See application file for complete search history.

(56) References Cited

U.S. PATENT DOCUMENTS

| | | | |
|---|---|---|---|
| 5,662,108 A | 9/1997 | Budd et al. | |
| 5,697,377 A | 12/1997 | Wittkampf | |
| 6,240,307 B1 | 5/2001 | Beatty et al. | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,187,973 B2 | 3/2007 | Hauck | |
| 7,189,208 B1 | 3/2007 | Beatty et al. | |
| 7,996,060 B2 | 8/2011 | Trofimov et al. | |
| 2003/0018251 A1 | 1/2003 | Solomon | |
| 2003/0078494 A1 | 4/2003 | Panescu et al. | |
| 2004/0254437 A1 | 12/2004 | Hauck et al. | |
| 2007/0049817 A1 | 3/2007 | Preiss et al. | |
| 2007/0299351 A1 | 12/2007 | Harlev et al. | |
| 2007/0299352 A1 | 12/2007 | Harlev et al. | |
| 2009/0076483 A1 | 3/2009 | Danehorn | |
| 2009/0262109 A1 | 10/2009 | Markowitz et al. | |
| 2009/0264778 A1* | 10/2009 | Markowitz ............ | A61B 5/053 600/508 |
| 2012/0059249 A1 | 3/2012 | Verard et al. | |
| 2014/0275991 A1 | 9/2014 | Potter et al. | |
| 2016/0045133 A1 | 2/2016 | Balachandran et al. | |
| 2016/0061599 A1 | 3/2016 | Zeng et al. | |
| 2020/0000368 A1 | 1/2020 | Ben-Haim et al. | |
| 2020/0085504 A1 | 3/2020 | Schwartz et al. | |
| 2020/0289025 A1 | 9/2020 | Dichterman et al. | |
| 2021/0128009 A1 | 5/2021 | Ben-Haim | |

FOREIGN PATENT DOCUMENTS

| | | | |
|---|---|---|---|
| CN | 105377135 | 3/2016 | |
| EP | 0974936 | 1/2000 | |
| EP | 0974936 B1 * | 1/2000 | ............ A61B 5/341 |
| EP | 1767166 | 3/2007 | |
| JP | 2003527164 A * | 9/2003 | ........... A61B 5/0538 |
| WO | WO 98/01069 | 1/1998 | |
| WO | WO-2006055286 A2 * | 5/2006 | ......... A61B 18/1492 |
| WO | WO 2008/097767 | 8/2008 | |
| WO | WO-2008097767 A2 * | 8/2008 | ........... A61B 5/6859 |
| WO | WO 2010/129095 | 11/2010 | |
| WO | WO 2011/142931 | 11/2011 | |
| WO | WO 2012/092016 | 7/2012 | |
| WO | WO-2014036439 A2 * | 3/2014 | ........... A61B 5/4836 |
| WO | WO 2014/118535 | 8/2014 | |
| WO | WO 2014/182822 | 11/2014 | |
| WO | WO 2016/033599 | 3/2016 | |
| WO | WO 2018/078540 | 5/2018 | |
| WO | WO 2018/130974 | 7/2018 | |
| WO | WO 2019/034944 | 2/2019 | |

OTHER PUBLICATIONS

Notification Regarding Third-Party Preissuance Submission dated Jan. 29, 2021 From the U.S. Patent and Trademark Office Re. U.S. Appl. No. 16/338,710.(2 Pages).
Third Party IDS Submission under 37 CFR 1.290 filed on Jan. 14, 2021 From the U.S. Patent and Trademark Office Re. U.S. Appl. No. 16/338,710.(2 Pages).
International Preliminary Report on Patentability dated Feb. 27, 2020 From the International Bureau of WIPO Re. Application No. PCT/IB2018/055344. (8 Pages).
International Preliminary Report on Patentability dated Feb. 27, 2020 From the International Bureau of WIPO Re. Application No. PCT/IB2018/056158. (8 Pages).
International Preliminary Report on Patentability dated May 9, 2019 From the International Bureau of WIPO Re. Application No. PCT/IB2017/056616. (8 Pages).
International Search Report and the Written Opinion dated Feb. 1, 2018 From the International Searching Authority Re. Application No. PCT/IB2017/056616. (14 Pages).
Crospon "Esophageal Treatment by Esoflip®", Crospon, Product Sheet, 4 P., 2017.
Crospon "Flip® Technology", Crospon, Product Sheet, 6 P., 2017.
Myronenko et al. "Non-Rigid Point Set Registration: Coherent Point Drift", Advances in Neural Information Processing Systems, NIPS, 19: 1009-1016, 2009.
International Preliminary Report on Patentability dated Jul. 25, 2019 From the International Bureau of WIPO Re. Application No. PCT/IB2018/050192. (8 Pages).
International Search Report and the Written Opinion dated May 9, 2018 From the International Searching Authority Re. Application No. PCT/IB2018/050192. (16 Pages).
International Search Report and the Written Opinion dated Nov. 30, 2018 From the International Searching Authority Re. Application No. PCT/IB2018/055344. (15 Pages).
Official Action dated Jun. 4, 2021 from the U.S. Patent and Trademark Office Re. U.S. Appl. No. 16/338,710. (22 pages).
Notification of Office Action and Search Report dated Jan. 11, 2022 From the State Intellectual Property Office of the People's Republic of China Re. Application No. 201880022135.4. (8 Pages).
Official Action dated Jan. 27, 2022 From the US Patent and Trademark Office Re. U.S. Appl. No. 16/484,501. (36 Pages).

* cited by examiner

SYSTEMS AND METHODS FOR RECONSTRUCTION OF INTRABODY ELECTRICAL READINGS TO ANATOMICAL STRUCTURE

RELATED APPLICATIONS

This application is a National Phase of PCT Patent Application No. PCT/IB2018/050192 having International filing date of Jan. 12, 2018, which claims the benefit of priority under 35 USC § 119(e) of U.S. Provisional Patent Application No. 62/445,433 filed on Jan. 12, 2017 and U.S. Provisional Patent Application No. 62/546,775 filed on Aug. 17, 2017. The contents of the above applications are all incorporated by reference as if fully set forth herein in their entirety.

PCT Patent Application No. PCT/IB2018/050192 is also related to U.S. Provisional Patent Application No. 62/412,324, filed on Oct. 25, 2016, the contents of which are incorporated herein by reference in their entirety.

FIELD AND BACKGROUND OF THE INVENTION

The present invention, in some embodiments thereof, relates to the field of navigation of body cavities by intrabody probes, and more particularly, to reconstruction of body cavity shape from measurements by intrabody probes.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems.

SUMMARY OF THE INVENTION

There is provided, in accordance with some embodiments of the present disclosure, a method of reconstructing a body cavity shape of a subject based on intrabody measurements of a plurality of crossing electromagnetic fields established within the body cavity, the method comprising: receiving measurements of the crossing electromagnetic fields using two sensors carried on an intrabody probe at a known distance from each other, the measuring being carried out with the probe at multiple locations in the body cavity; and reconstructing a shape of the body cavity, based on the received measurements; wherein the reconstructing comprises assigning the measurements of the crossing electromagnetic fields to locations so that variability in distances between sister locations is minimized, wherein sister locations are locations assigned to sister measurements, and sister measurements are measurements of the crossing electromagnetic fields measured substantially simultaneously by two sensors carried on the intrabody probe at the known distance from each other.

In some embodiments, the criterion of reducing variability reduces differences between distances of sister locations and the known distance.

In some embodiments, the reconstructing comprises assigning the measurements to locations in a segmentation preserving manner.

In some embodiments, the reconstructing comprises assigning the measurements to locations by a measurement-to-location transform decomposable to components of different spatial frequencies, and minimizing high frequency components of the transform.

In some embodiments, the measurements are taken by three or more sensors.

In some embodiments, at least the distance between two of the three or more sensors is unknown.

In some embodiments, the intrabody probe sensors comprise electrodes.

In some embodiments, the sensors measure voltage.

In some embodiments, the measurements include voltage measurements.

In some embodiments, the voltage indicates impedance.

In some embodiments, the measurements include impedance measurements.

In some embodiments, the intrabody probe comprises more than two sensors fixed to a rigid portion of the intrabody probe at predetermined distances from one another.

In some embodiments, the intrabody probe is flexible to change distances between the sensors, and the method comprises measuring at least one parameter indicative of bending of the intrabody probe, and wherein the positions of the plurality of sensors used in the reconstructing are adjusted based on the parameter indicative of bending.

In some embodiments, the positions of the sensors comprise an arrangement of the sensors along a plurality of segments of the intrabody probe, at predetermined distances from one another, wherein the segments are configured to open to a spread configuration to the predetermined distances.

In some embodiments, the plurality of crossing electromagnetic fields comprise at least one electromagnetic field established between electrodes of the sensors.

In some embodiments, the method comprises receiving data indicative of measurements of at least one parameter varying in time together with a change in the body cavity shape; wherein reconstructing comprises using the data indicative of the at least one parameter to reduce an effect of the change in the body cavity shape on the reconstruction.

In some embodiments, the at least one parameter varying in time comprises a heartbeat phase of the subject.

In some embodiments, the at least one parameter varying in time comprises a respiratory phase of the subject.

In some embodiments, reconstructing comprises minimizing the volume in physical space, to which static measurements are transformed, wherein static measurements are measurements measured when the intrabody probe is immobilized against a moving tissue of the body cavity.

There is provided, in accordance with some embodiments of the present disclosure, an apparatus for reconstructing a body cavity shape of a subject based on intrabody measurements of a plurality of crossing electromagnetic fields established within the body cavity, the method comprising: computer circuitry, configured to receive measurements of the crossing electromagnetic fields using two sensors carried on an intrabody probe at a known distance from each other, the measuring being carried out with the probe at multiple locations in the body cavity; and reconstruct a shape of the body cavity, based on the received measurements by assigning the measurements of the crossing electromagnetic fields to locations so that variability in distances between sister locations is minimized, wherein sister locations are locations assigned to sister measurements, and sister measurements are measurements of the crossing electromagnetic fields measured substantially simultaneously by two sensors carried on the intrabody probe at the known distance from each other.

In some embodiments, the computer circuitry is configured to minimize differences between distances of sister locations and the known distance to reconstruct the shape of the body cavity.

In some embodiments, the computer circuitry is configured to assign the measurements to locations in a segmentation preserving manner.

In some embodiments, the computer circuitry is configured to assign the measurements to locations by a measurement-to-location transform decomposable to components of different spatial frequencies, after minimizing high frequency components of the transform.

In some embodiments, the apparatus further comprises the intrabody probe.

In some embodiments, the intrabody probe comprises three or more sensors.

In some embodiments, at least a distance between two of the three or more sensors is unknown.

In some embodiments, the intrabody probe sensors comprise electrodes.

In some embodiments, the sensors measure voltage.

In some embodiments, the intrabody probe comprises more than two sensors fixed to a rigid portion of the intrabody probe at predetermined distances from one another.

In some embodiments, the plurality of crossing electromagnetic fields comprise at least one electromagnetic field established between electrodes of the sensors.

In some embodiments, the computer circuitry is configured to receive data indicative of measurements of at least one parameter varying in time together with a change in the body cavity shape; and use the data indicative of the at least one parameter to reduce an effect of the change in the body cavity shape on the reconstruction.

In some embodiments, the computer circuitry is configured to minimize a volume in physical space, to which static measurements are transformed, wherein static measurements are measurements measured when the intrabody probe is immobilized against a moving tissue of the body cavity.

There is provided, in accordance with some embodiments of the present disclosure, a method of reconstructing a shape of a body cavity of a subject based on intrabody measurements of a plurality of crossing electromagnetic fields established within the body cavity, the method comprising: receiving measurements of the crossing electromagnetic fields, taken with a probe at different locations within the body cavity of the subject using two sensors mounted on the probe at a known distance from each other; and reconstructing a shape of the body cavity, based on the measurements received; wherein the reconstructing comprises using a segmentation-preserving transform to assign a position to each of the two sensors at each of the different locations of the probe based on the measurements received, and the known distance.

In some embodiments, the reconstructing comprises assigning the measurements to locations by a measurement-to-location transform decomposable to components of different spatial frequencies, and minimizing high frequency components of the transform.

In some embodiments, the measurements are taken by three or more sensors.

In some embodiments, at least the distance between two of the three or more sensors is unknown.

In some embodiments, the intrabody probe sensors comprise electrodes.

In some embodiments, the intrabody probe comprises a more than two sensors arranged on a rigid portion of the intrabody probe at predetermined distances from one another.

In some embodiments, the intrabody probe is flexible to change distances between the sensors, and the method comprises measuring at least one parameter indicative of bending of the intrabody probe, and wherein the positions of the plurality of sensors used in the reconstructing are adjusted based on the parameter indicative of bending.

In some embodiments, the positions of the plurality of sensors comprise an arrangement of the sensors along a plurality of segments of the intrabody probe, at predetermined distances from one another, wherein the segments are configured to open to a spread configuration to the predetermined distances.

In some embodiments, the plurality of crossing electromagnetic fields comprise at least one electromagnetic field established between electrodes of the sensors.

In some embodiments, reconstructing comprises using the data indicative of the at least one parameter to reduce an effect of the change in the body cavity shape on the reconstruction.

In some embodiments, the at least one parameter varying in time comprises a heartbeat phase of the subject.

In some embodiments, the at least one parameter varying in time comprises a respiratory phase of the subject.

In some embodiments, reconstructing comprises minimizing the volume in physical space, to which static measurements are transformed, wherein static measurements are measurements measured when the intrabody probe is immobilized against a moving tissue of the body cavity.

There is provided, in accordance with some embodiments of the present disclosure, a method of reconstructing a body cavity of a subject based on intrabody measurements of a plurality of crossing electromagnetic fields established within the body cavity, the method comprising: receiving measurements of crossing electromagnetic fields, taken with a intrabody probe at different locations within the body cavity of the subject using two sensors mounted on the probe at a known distance from each other; and reconstructing a shape of the body cavity, based on the measurements received; wherein the reconstructing comprises assigning a position to each of the two sensors at each of the different locations of the probe based on the measurements received, the known distance, and a coherence constraint on assignments of the locations to the field measurements.

In some embodiments, the measurements are taken by three or more electrodes, and not all the distances between the electrodes are known.

In some embodiments, the intrabody probe sensors comprise electrodes.

In some embodiments, the sensors measure voltage.

In some embodiments, the voltage indicates impedance.

In some embodiments, the intrabody probe is a catheter probe.

In some embodiments, the body cavity comprises a chamber of a mammalian heart.

In some embodiments, the plurality of crossing electromagnetic fields comprise a plurality of time-varying electromagnetic fields crossing within the body cavity, whereby each region in the cavity is characterized by a distinct set of voltage values with respect to the time-varying electromagnetic fields.

In some embodiments, the reconstructing the body cavity shape comprises associating properties of tissues surrounding the body cavity to positions of the reconstructed body cavity shape.

In some embodiments, the associating comprises associating the measured property to a position of the reconstructed body cavity shape.

In some embodiments, the positions of the reconstructed body cavity shape associated to properties of tissues comprise positions of a periphery of the reconstructed body cavity shape.

In some embodiments, the intrabody probe comprise two or more sensors arranged on a rigid portion of the intrabody probe at predetermined distances from one another.

In some embodiments, the intrabody probe is flexible to change distances between the sensors, comprising measuring at least one parameter indicative of bending of the intrabody probe, and wherein the positions of the plurality of sensors used in the reconstructing are adjusted based on the parameter indicative of bending.

In some embodiments, the positions of the sensors comprise an arrangement of sensors along a plurality of segments of the intrabody probe, at predetermined distances from one another, wherein the segments are configured to open to a spread configuration to the predetermined distances.

In some embodiments, the plurality of crossing electromagnetic fields comprise at least four electromagnetic fields established from body surface electrodes, and intersecting within the body cavity.

In some embodiments, the plurality of crossing electromagnetic fields comprise at least one electromagnetic field established between electrodes of the sensors.

In some embodiments, reconstructing comprises using the data indicative of the at least one parameter to reduce an effect of the change in the body cavity shape on the reconstruction.

In some embodiments, the at least one parameter varying in time comprises a heartbeat phase of the subject.

In some embodiments, the at least one parameter varying in time comprises a respiratory phase of the subject.

In some embodiments, reconstructing comprises minimizing the volume in physical space, to which static measurements are transformed, wherein static measurements are measurements measured when the intrabody probe is immobilized against a moving tissue of the body cavity.

There is provided, in accordance with some embodiments of the present disclosure, a method of reconstructing a shape of a body cavity of a subject based on intrabody measurements of a plurality of crossing electromagnetic fields established within the body cavity, the method comprising: receiving measurements of the crossing electromagnetic fields, taken with a probe at different locations within the body cavity of the subject using two sensors mounted on the probe at a known distance from each other; and reconstructing a shape of the body cavity, based on the measurements received and the known distance; wherein the reconstructing comprises using a transform to assign a position to each of the two sensors at each of the different locations of the probe based on the measurements received, wherein the transform is constrained to minimize high spatial frequency components of a spatial distribution of distance between sister locations generated by the transform, wherein sister locations are locations assigned to sister measurements, and sister measurements are measurements of the crossing electromagnetic fields measured substantially simultaneously by two sensors carried on the intrabody probe at the known distance from each other.

In some embodiments, the reconstructing comprises assigning the measurements of the crossing electromagnetic fields to locations so that distances between sister locations change across the body cavity reconstruction according to a criterion of reducing variability in distances between sister locations.

In some embodiments, the measurements are taken by three or more sensors.

In some embodiments, at least the distance between two of the three or more sensors is unknown.

In some embodiments, the intrabody probe sensors comprise electrodes.

In some embodiments, the intrabody probe comprise two or more sensors arranged on a rigid portion of the intrabody probe at predetermined distances from one another.

In some embodiments, the intrabody probe is flexible to change distances between the sensors, and the method comprises measuring at least one parameter indicative of bending of the intrabody probe, and wherein the positions of the plurality of sensors used in the reconstructing are adjusted based on the parameter indicative of bending.

In some embodiments, the positions of the plurality of sensors comprise an arrangement of the sensors along a plurality of segments of the intrabody probe, at predetermined distances from one another, wherein the segments are configured to open to a spread configuration to the predetermined distances.

In some embodiments, the plurality of crossing electromagnetic fields comprise at least one electromagnetic field established between electrodes of the sensors.

In some embodiments, reconstructing comprises using the data indicative of the at least one parameter to reduce an effect of the change in the body cavity shape on the reconstruction.

In some embodiments, the at least one parameter varying in time comprises a heartbeat phase of the subject.

In some embodiments, the at least one parameter varying in time comprises a respiratory phase of the subject.

In some embodiments, reconstructing comprises minimizing the volume in physical space, to which static measurements are transformed, wherein static measurements are measurements measured when the intrabody probe is immobilized against a moving tissue of the body cavity.

There is provided, in accordance with some embodiments of the present disclosure, a method of reconstructing a body cavity shape of a subject based on intrabody measurements of a plurality of crossing electromagnetic fields established within the body cavity, the method comprising: receiving measurements of the crossing electromagnetic fields using two sensors carried on an intrabody probe at a known distance from each other, the measuring being carried out with the probe at multiple locations in the body cavity; receiving data indicative of measurements of at least one parameter varying in time together with a change in the body cavity shape; and reconstructing a shape of the body cavity, based on the received measurements; wherein the reconstructing comprises assigning the measurements of the crossing electromagnetic fields to locations using a transform that minimizes a volume in physical space, to which static measurements are transformed, wherein static measurements are measurements measured when the intrabody probe is immobilized against a moving tissue of the body cavity.

In some embodiments, the transform further minimizes variability in distances between sister locations across the body cavity reconstruction; wherein sister locations are locations assigned to sister measurements, and sister measurements are measurements of the crossing electromagnetic fields measured substantially simultaneously by two sensors carried on the intrabody probe at a known distance from each other.

There is provided, in accordance with some embodiments of the present disclosure, a method of reconstructing a body cavity shape of a subject based on intrabody measurements of voltages within a plurality of crossing electromagnetic fields established within the body cavity, the method comprising: measuring voltages from a plurality of mutually spaced sensors carried on an intrabody probe; and reconstructing a shape of the body cavity, based on the measuring; wherein the reconstructing comprises assigning the measured electromagnetic field voltages to reconstructed body cavity shape positions based on both: positions of the plurality of mutually spaced sensors relative to one another, and at least one criterion for spatial coherence of the measured electromagnetic field voltages assigned to positions in the reconstructed body cavity shape.

According to some embodiments of the present disclosure, the intrabody probe sensors comprise electrodes.

According to some embodiments of the present disclosure, the intrabody probe is a catheter probe.

According to some embodiments of the present disclosure, the body cavity comprises a chamber of a mammalian heart.

According to some embodiments of the present disclosure, the plurality of crossing electromagnetic fields comprise a plurality of time-varying electromagnetic fields crossing within the body cavity, whereby each region in the cavity is characterized by a distinct set of voltage values with respect to the time-varying electromagnetic fields.

According to some embodiments of the present disclosure, the reconstructing a shape of the body cavity comprises associating properties of tissues surrounding the body cavity to positions of the reconstructed shape.

According to some embodiments of the present disclosure, the associating comprises associating the measured property to a position of the reconstructed shape.

According to some embodiments of the present disclosure, the positions of the reconstructed shape comprise positions at the walls of the reconstructed shape.

According to some embodiments of the present disclosure, the positions of the plurality of mutually spaced sensors comprise a linear arrangement of the sensors at predetermined distances from one another along the intrabody probe.

According to some embodiments of the present disclosure, the intrabody probe is flexible to change distances between the mutually spaced sensors, comprising measuring at least one parameter indicative of bending of the intrabody probe, and wherein the positions of the plurality of mutually spaced sensors used in the reconstructing are adjusted based on the parameter indicative of bending.

According to some embodiments of the present disclosure, the positions of the plurality of mutually spaced sensors comprise an arrangement of the sensors along a plurality of segments of the intrabody probe, at predetermined distances from one another, wherein the segments are configured to open to a spread configuration to the predetermined distances.

According to some embodiments of the present disclosure, the plurality of crossing electromagnetic fields comprise at least four electromagnetic fields generated from body surface electrodes, and crossing within the body cavity.

According to some embodiments of the present disclosure, the plurality of crossing electromagnetic fields comprise at least one electromagnetic field generated between electrodes of the mutually spaced sensors.

According to some embodiments of the present disclosure, reconstructing comprises using the time-varying parameter to link the electromagnetic field voltages to a particular state of the changing body cavity shape.

According to some embodiments of the present disclosure, the at least one time-varying parameter comprises a heartbeat phase of the subject.

According to some embodiments of the present disclosure, the at least one time-varying parameter comprises a respiratory phase of the subject.

According to some embodiments of the present disclosure, the at least one time-varying parameter comprises one or more of the group consisting of: hydration state of the subject, heart rate of the subject, and edematous state of tissue surrounding the body cavity.

According to some embodiments of the present disclosure, a particular state of the changing body cavity shape is at least partially reconstructed based on electromagnetic field voltages measured while the intrabody probe is immobilized relative to a portion of the body cavity shape, including being reconstructed based on a constraint linking positions of the electromagnetic field voltages to positions of the portion of the body cavity shape.

According to some embodiments of the present disclosure, a particular state of changing body cavity shape is at least partially reconstructed based on comparing electromagnetic field voltages measured in a measured region while the intrabody probe is immobilized relative to a portion of the body cavity shape with electromagnetic field voltages measured in the same measured region while the intrabody probe is not so-immobilized.

According to some embodiments of the present disclosure, a particular state of the changing body cavity shape is at least partially determined based on a shape of the body cavity modeled for conditions indicated by the at least one time-varying parameter.

According to some embodiments of the present disclosure, the reconstructing comprises using a simulation of the differently-oriented electromagnetic fields established within the body to constrain linkage of the time-varying parameter to the electromagnetic field voltages to a particular state of the changing body cavity shape.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system" (e.g., a method may be implemented using "computer circuitry"). Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
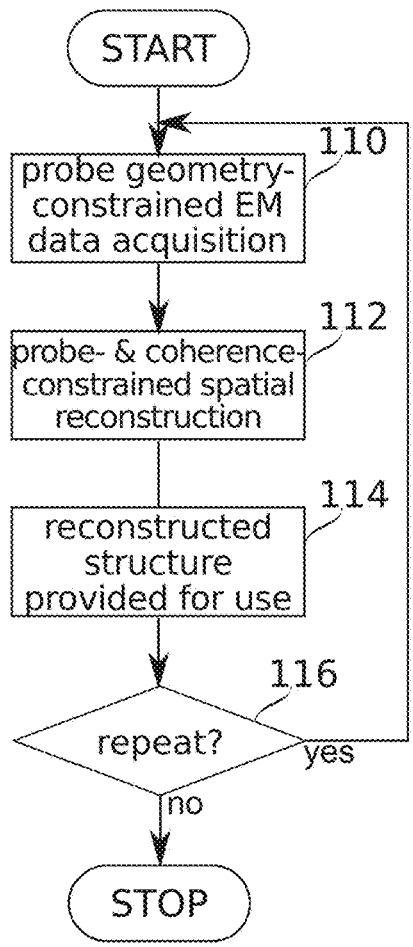
FIG. 1A is a schematic flowchart of a method for reconstructing a body cavity map using an intrabody probe, according to some exemplary embodiments of the present disclosure.

The present invention, in some embodiments thereof, relates to the field of navigation of body cavities by intrabody probes, and more particularly, to reconstruction of body cavity shape from measurements by intrabody probes.

Overview

An aspect of some embodiments of the present invention relates to reconstruction of a body cavity shape of a subject (e.g., a patient undergoing a catheterization procedure) based on measurements from a plurality of sensors (e.g., an intrabody probe carrying a plurality of sensors such as electrodes occupying known spaced positions relative to the geometry of the intrabody probe). In some embodiments, the reconstruction process is guided by known spatial constraints on the relative positions of the plurality of sensors. Optionally, local spatial calibration defined by the spatial constraints is used in combination with constraints on the spatial coherence of measurements as part of the reconstruction process. The concept of spatial coherence is explained in passages under the subtitle "Coherence constraints on reconstruction".

As used herein, the term "reconstruction" is used (as are related word forms, e.g., "reconstruct" and "reconstructing") to indicate a process of and/or process product from the generation of a representation of a three dimensional (3-D) shape of a target, based on position data used as indications of positions within the target. Herein, positions "within" a target should be understood to include periphery and/or surface positions of the target.

In some embodiments, reconstruction comprises mapping from a set of measurements in a position data space (e.g., measurements of a plurality of distinguishable electromagnetic fields, wherein each of the fields contributes at least one dimension to the position data space) to corresponding positions in a physical space at which those measurements are made. The collection of measurements is optionally referred to as a "V cloud"; that is, a cloud of measurements in measurement space. In some embodiments, voltage measurements and/or impedance measurements may serve as measurements of the electromagnetic fields (optionally, measurements of time-varying voltage are used as indications of impedance). More generally, every parameter characterizing the electromagnetic field may serve to measure the electromagnetic fields. Herein, the term "physical space" is used to refer to the range of physical locations over which the target extends, and the term "measurement space" is used to refer to the range over which the measurements extend. The physical space is at least three-dimensional, as it has height, width, and depth (and optionally also time), and the dimensionality of the measurement space depends on the number of frequencies used for the measurements, where each frequency corresponds to one dimension. The collection of positions in the physical space, to which the measurements making the V cloud are transformed, is optionally referred to as an "R cloud". In some embodiments, the 3-D shape of the reconstruction is represented as a 3-D mesh, for example, a 3-D mesh that bounds all the positions in the R cloud. Optionally, the 3-D mesh is defined by the path of a sphere or other geometrical shape sliding over the R cloud; wherein the size of the sphere defining how deeply the sphere can penetrate between mesh points, so that the mesh surface is made relatively smooth.

In some embodiments of the present invention, the target whose shape is to be reconstructed, generally referred to herein as "the target" is a body cavity; wherein the positions indicated by the position data comprise positions within the body cavity shape. The reconstructed representation models at least the target's shape. Optionally, the reconstructed representation represents additional target properties associated with the target shape, for example, tissue type, electrical and/or dielectric properties, or another property.

The process of reconstruction is optionally supplemented by further information such as a template shape that is transformed to match available position data and/or used as a template shape to which available position data are transformed. In some embodiments, the reconstructed representation comprises and/or is presentable as an image of the target shape. For example, a reconstructed 3-D representation modeling a body cavity is rendered to an image of the body cavity using 3-D rendering software. Optionally, a reconstructed 3-D representation is subject to pre-processing transformation of its position data (e.g., unwrapping, flattening, or another transformation) before production of an image of the reconstructed representation.

The term "position data" is used herein to refer generally to data used to determine spatial positions. In some embodiments, at least some of the position data used are obtained in the form of measurements of one or more physical characteristics of the tissue environment at a probe's current position. The probe, in some embodiments, is an electrode probe, and the measurements are electrical measurements. Additionally or alternatively, position data comprises image data. Position data can also be provided as constraints, e.g., to provide context to other position data and help in defining the spatial position that the position data indicates.

Herein the term "constraint" is used in several descriptions to refer to conditions imposed on a transformation from measurement space to physical space. The constraints may reflect information and/or assumptions that limit possible measurements, locations (in physical space), and relationships between measurements and locations. Constraints are optionally not used as "hard constraints", i.e., sometimes, they may not be fully obeyed, e.g., simultaneous measurements from a plurality of electrodes may be "constrained" to be assigned to locations separated by fixed distances from each other, but in practice may be assigned to locations of slightly different distances. This may occur due, for example, to measurement errors, competing constraints, features of an algorithm used for minimization of error in assigned positions, etc. As used herein, the term "to minimize" and its inflections (such as minimizing, minimization, etc.) refer to attempt to reach a smallest possible value under given conditions, but does not guarantee that the attempt is fully successful. For example, in some embodiments, minimization is carried out iteratively with a convergence criterion, determining when to stop the iterations. Applying a different convergence criterion may lead to a smaller value (e.g., by spending on the minimization longer computation time). Still, the value obtained is referred to as minimized, although a smaller value could have been found, for example, by a different minimization mechanism, by a different convergence condition, etc.

In some embodiments, the intrabody probe is a catheter probe moved within the body cavity (e.g., a heart chamber such as an atrium of a mammalian heart) to different positions at which sets of measurements are taken from the plurality of sensors. Such "sets" are optionally taken to be comprised of measurements taken at substantially the same time and/or while the catheter probe remains substantially in a same position, so that members of each set may be related to one another through application of mutual position constraints (such as known relative distance).

The plurality of sensors, in some embodiments, are probe-borne detection elements of measurement-taking devices; e.g., electrodes, or another device, for example, magnetic field sensor, sound field detector, photon detector, or the like. Sensor-produced position data suitable for use with some embodiments of the current invention comprise sensed data which "tags" or otherwise helps identify particular positions occupied by the data-acquiring sensor. In some embodiments, the identifying is based on sensing positions within one or more artificially established fields of electrical voltages, sound (e.g., ultrasound), magnetic forces, electromagnetic radiation, particle radiation, and/or another field. Herein, electrode-based sensing of electrical voltages is used as a main example, but it should be understood that other position sensing methods are optionally used with methods described herein, changed as necessary.

The measurements are of one or more parameters treated singly or in combination as identifying of particular locations within the body cavity for purposes of reconstruction. Optionally, the parameters are treated as being identifiers of particular locations under particular conditions (e.g., heartbeat phase and/or respiratory phase). In some embodiments, the measurements comprise measurements of voltages within crossed, time-varying electromagnetic fields. To distinguish the fields, in some embodiments, the crossed electromagnetic fields vary at distinguishable frequencies. As used herein, crossed or crossing fields are fields directed in directions that are not parallel to each other, nor antiparallel, so that the direction of each field crosses the directions of all the other fields. Crossing fields may allow assigning to each point in space a unique combination of field values, provided the number of the crossing fields is not smaller than the dimensionality of the space. Thus, for mapping a three dimensional space, at least three crossing fields are required, and more may be used. A larger number of crossing fields may provide information usable, for example, for noise reduction and improvement of robustness in comparison to robustness achievable with only three crossing fields. The voltage gradients of the crossed electromagnetic fields are used, in some embodiments, to define axes indicating spatial position as a function of measured voltage. Since the voltage gradients are ordinarily curved, and/or otherwise irregular, the conversion to axis-defined position generally relies on the use of some form of transformation. Optionally, the transformation is dynamic (e.g., changing as a function of contact quality, movement artifacts, and the like).

In some embodiments, the body cavity shape is reconstructed to obtain a representation of a void region limited in its extents by surrounding tissue (e.g., a heart chamber, vascular lumen, gastrointestinal space, and/or urinary tract lumen). Additionally or alternatively, properties of the surrounding tissue are also included in the reconstruction, for example by associating additional measurements to positions at boundaries of the body cavity shape. The additional measurements may be additional to the electromagnetic field measurements, for example, measurements of electrical activity. Properties can include measured states of tissue such as myocardial electrical activity, dielectric properties of tissue, nearby locations of hard, soft, and/or void-filled body structures, etc.

In some embodiments, reconstruction of a body cavity shape and/or navigation in a body cavity using the reconstruction may be obtained by calculating a transform function $T(x)$ for each measurement x in a set of measurements X to obtain Y; which may be, for example, a reconstruction of a body cavity (e.g., if reconstruction is sought) or a position within a reconstruction (e.g., if navigation is to be guided). Measurements X may comprise measurements taken from a plurality of different sensors (e.g. electrodes) mounted on a probe moved within the body cavity. A transform function transforming measurements in measurement space to locations in physical space may be referred to herein as a measurement-to-location transform.

In some embodiments, a pre-acquired image and/or other data of the body cavity may be available, e.g., a CT image of the body cavity, and used for the reconstruction and/or navigation in the body cavity. For example, it may be used for simulating expected voltage gradients at different regions in the target, and this identification may be used as a constraint on the transform, e.g., that when a given voltage gradient (e.g., between two electrodes) is measured, a transform transforming it to a region where the same (or similar) gradient was simulated to exist will be preferred over transforms transforming it to other regions.

In some embodiments, methods described herein for reconstruction may be used to update a pre-acquired image of a body part (e.g., a pre acquired anatomical image, for example a CT image) to account for changes occurring in the body part from the time when the image was acquired. For example, after a CT image was obtained, the patient may be treated (e.g., by providing medicine or other procedures) which may change the body part (e.g., expand or contract—the heart, for example, can change average size as a function of heartbeat rate, instantaneous size as a function of heartbeat cycle, or for other reasons), such change may be calculated, e.g., based on a set of measurements of the changed body part. The calculated change may be applied to the pre-acquired anatomical image to reconstruct an updated anatomical image which may correspond to a current state of the body part. There may also be updating of a previous reconstruction carried out by a different intrabody probe mapping method, optionally the same mapping method.

In some embodiments, reconstruction of a body cavity shape, and/or navigation in a body cavity (which may be guided based on a reconstruction), optionally comprises imposing different constraints on how the reconstruction should be performed using the set of measurements. The constraints may include, for example, any suitable constraint described herein or combination of two or more thereof. One or more of the constraints described in relation to reconstruction of a body part may be used for navigation in a body part, e.g., navigation of a probe in the part during a diagnosis and/or treatment procedure.

Local Spatial Position Constraints on Reconstruction

In some embodiments, reconstruction of a body cavity shape and/or navigation in a body cavity may be obtained by first assuming local spatial position constraints which are consistent with the physical conditions applying to individual sets of measurements (like the known relative distance of measuring sensors at the time the measurements were taken). In some embodiments, this assumption is combined with use of a multidimensional scaling (MDS) algorithm. MDS algorithms refer to a class of algorithms wherein objects (in some embodiments, measurements of voltage) are placed in an N-dimensional space (e.g., as described herein, the three dimensional space of a body cavity) so that between-object distances are preserved as well as possible (given all other, potentially competing, constraints). In some embodiments, the geometrical configuration of sensors on an intrabody probe provides the between-object distances, allowing an MDS approach to be used for reconstruction of a body part.

In some embodiments, each set of measurements comprises measurements taken from a plurality of different measurement locations on the probe (e.g., measurement locations defined by sensor locations, for example: electrodes mounted on the probe); measurements taken substantially simultaneously and/or while the probe remains in substantially the same position. Moreover, in some embodiments, the different measurement locations on the probe have known spatial relationships to one another, which comprise, in some embodiments, local spatial position constraints. Reconstruction of the body cavity shape may be guided based on these known spatial relationships; for example, in some embodiments, a transform function T(x) on a set of measurements X may be calculated such that $|T(x_i)-T(x_j)| \approx d_{ij}$; $d_{ij}$ being the distance between electrode$_i$ and electrode$_j$.

For example, in some embodiments, the electrodes are each at a known distance and/or angle from one another due to a fixed geometry of the intrabody probe to which they are mounted. Alternatively, in some embodiments, electrodes are in variable relative positions, and the variation accounted for based on information such as parameters of deployment (e.g., how expanded a basket-shaped intrabody probe is at a moment of measurement), and/or on further measurements (for example, of force as an indication of probe deformation, inter-electrode conductance as an indication of inter-electrode distance, etc.). Optionally, additional constraints on the relative orientation of the measurement locations are also used. Such constraints are optionally known, for example, from geometrical/anatomical constraints on the procedure itself.

Optionally, measurements in each set are substantially simultaneous. Herein, "substantially simultaneous" should be understood to mean that the measurements of each set may be obtained:

actually simultaneously (i.e., with partially or wholly overlapping measurement periods), close enough in time that motions of the intrabody probe during acquisition of the set can be neglected, and/or close enough in time that skew due to small movements during sampling of a set of measurements can be dependably factored out and/or adjusted for if necessary (e.g., by use of time-weighted averaging of time-adjacent samples).

Optionally, a collection of measurements is considered as a set of measurements mutually constrained in relative position (e.g., fixed at particular relative distances and/or relative angles, at variable but known distances or angles, for example by use of an encoder, etc.), without a requirement for substantial simultaneity of measurement. For example, multiple measurements at multiple times from an intrabody probe are optionally taken while a portion of the intrabody probe remains anchored at one or more regions. Relative movements of other intrabody probe portions, assuming they are known (by use of a movement encoder, for example) can then be applied to determine a relative position constraint. These measurements are optionally related to one another through use of the fixed anchor and the known bending parameters to provide calibration. It can be understood from this, and it should be understood to apply generally, that a measurement optionally is treated as a member of a plurality of "sets" of measurements, where members of each set may be related to one another through application of different mutual position constraints.

For simplicity, and for purposes of description herein, sets of simultaneous measurements from corresponding electrodes of a fixed-shape probe are often used in examples.

However, it should be understood that other configurations of sensors, and/or other methods of obtaining a spatially calibrated "ruler" to constrain distances between them are optionally used in some embodiments of the present invention. In some embodiments, the constrained distances may be used to ensure that the target shape is reconstructed so that the distance between the electrodes (e.g., in mm) is kept approximately the same all around the reconstructed shape, even if the difference between their readings (e.g., in mV) changes substantially from one place to another. For example, in some embodiments, the length of the catheter is reconstructed to be the same within ±15% even though the voltage gradient between the same electrodes changes by a factor of 10 or more.

Coherence Constraints on Reconstruction

In some embodiments, reconstruction of a body cavity shape and/or navigation in a body cavity using such a reconstruction may be obtained by imposing coherence constraints, e.g., a coherence model, on a set of measurements.

In some embodiments of the invention, the coherence constraints are added to constraints on relative positions assigned to sensors (e.g., electrode positions). For example: two measurements made at nearby regions in space are assumed to produce measurement values which are also "nearby" under some metric. Similarly, the transformation of measurements to locations may be constrained so that every two measurements of "nearby" values are transformed to locations close to each other, under some metric. In some embodiments, voltages measured substantially simultaneously by two electrodes separated from each other by a fixed distance (e.g., because they are fixed to a rigid probe portion), may be referred to as sister measurements; the locations assigned to such measurements may be referred to as sister locations; and the distances between sister locations may be referred to as sister distances. A coherence criterion may be set to require that sister distances change smoothly across the body cavity. An algorithm for finding a transformation that generates smooth changes in sister distances may be obtained, for example, when the spatial distribution of sister distances is decomposable to components having different spatial frequencies. The algorithm then may penalize transformations generating sister-distance-distribution of high frequency components, and the overall penalty may be minimized (by reducing the contribution of high frequency components to the distribution of sister distances) in order to find a coherent transformation. For example, a penalty may be set to each component, and the penalty may increase as the frequency of the component increases. This way, distributions that include only low frequency components would nearly not be penalized, and those that include components of very high frequencies will be penalized heavily. A minimization procedure may be applied to minimize the penalty, to find a transformation that results in sister distances that change smoothly (i.e., with mainly small frequency components), which is an example of a coherence criterion. Additionally, a coherence criterion is optionally influenced by the direction of voltage gradient (i.e., a smaller change in gradient direction is "more coherent"), and/or by the rate of change in the gradient itself (and/or its direction) and/or any higher order gradient derivative.

The metric by which distances are measured for defining coherence, can be, for example, the Euclidean distance. In some embodiments, the metric may be a "natural" distance, as this is explained below. In some embodiments, the metric may be a distance in a measurement-defined vector space (i.e., a vector space comprising a plurality of different measured parameters as vector components), but may also be more involved than that.

More generally, the coherence constraint can be expressed as $\Delta X_{ij} \propto \Delta Y_{ij}$, where $\Delta X_{ij}$ is a change between two locations i, j of measured values in X (for example, changed measurements of voltage with respect to a plurality of crossed voltage gradient-defined axes), and $\Delta Y_{ij}$ is a change in the spatial position (e.g., distance, under a suitable metric) between the two locations i, j, within the body cavity to be reconstructed, Y.

The proportionality sign $\propto$ should be understood to refer to any suitable coherence metric and/or algorithm (coherence model), not necessarily constant uniform proportionality. For example, a proportionality parameter is optionally allowed to vary over the domain of measurement values. In some embodiments, the coherence model allows the proportionality parameter to vary smoothly, and/or according to a model of expected behavior, e.g., varying smoothly everywhere except near the edges or other particular zones of the mapped space.

In either physical space or measurement space, distances are not necessarily direct Euclidean distances. In some embodiments, for example, the measurements may form a measurement cloud (in some measurement vector space, for example), and the spatial positions to which the measurements are transformed may form a position cloud. In some embodiments, a natural distance between two measurements may be defined as the length of the shortest path that goes between the two measurements only through the measurement cloud. A path going only through a cloud is referred to herein as an intra-cloud path. Similarly, a natural distance between two spatial positions may be defined as the length of the shortest path that goes between the two spatial positions only through the position cloud (that is, the shortest intra-cloud path in space). In some embodiments, the measurement cloud may be segmented, in the sense that it includes distinct segments; for example, a central segment connected to each of a plurality of peripheral segments. The peripheral segments may be interconnected only by pathways passing into the central segment from one segment, and back out of it to the other. In such embodiments, two peripheral segments may have points (e.g., measurements) that are nearby in the Euclidean sense, but the natural distance between them is long, as every intra-cloud path between them goes via the central segment. In such embodiments, measuring coherence using natural distances may preserve the segmentation of the measurement cloud, so that the position cloud remains similarly segmented. That is, a transform requiring coherence in terms of natural distances may transform a segmented measurement cloud into similarly segmented spatial positions cloud. Such a transform (whether based on intra-cloud coherence or preserving the segmentation by different means) may be referred to herein as a segmentation preserving transform. A segmentation preserving transform is potentially suitable to preserving features of heart chambers; for example, for preserving the pulmonary veins connected to the left atrium and separated from each other.

An example of a segmentation preserving method of transforming a segmented measurement cloud into a similarly segmented position cloud may include steps of assigning each measurement to a segment in the measurement cloud; and transforming each measurement to a position in a segmented spatial position cloud requiring that measurements assigned to a same segment in the measurement cloud are transformed to a same segment in spatial position cloud and measurements assigned to different segments in the measurement cloud are transformed to different segments in the spatial position cloud. Such segmentation preserving method may replace a Euclidean-distance based coherence condition, or be used in addition. For example, in some embodiments, the coherence may be primarily based on Euclidean distances, with segment preservation used to protect against segments coalescing, e.g., by disallowing influence on the coherence model by differences between points whose Euclidean distance is sufficiently shorter than their natural distance.

Combination of Spatial and Coherence Constraints

In some embodiments, the approaches of local spatial constraint (MDS) and the coherence-constraint are used in a combined method of reconstruction. Outputs of each are optionally reconciled by use of an error (or "energy") reducing weighting scheme, for example as now described.

Initially, in some embodiments, the detailed, or optionally even the overall geometry defined by a "true" body cavity shape Y is unknown, but still, a useful approximation may be obtained by a transformation that transforms the measurements according to the applied constraints. The target for "usefulness" is optionally dependent on the particulars of the procedure, and even of particular tasks within the procedure; and there can be a plurality of criteria for evaluating the accuracy of reconstruction. In some embodiments, for example, the target for "useful approximation" is to be able to place adjacent small lesions next to each other within some relative margin of error as part of an ablation procedure; for example, an error within 0.5 mm, 1 mm, 2 mm, 4 mm, or some other intermediate margin of error. Additionally or alternatively, another target for useful approximation is positioning a linked chain (or other grouping) of small lesions within some margin of error relative to landmarks of a target tissue; for example, an error within 1 mm, 2 mm, 4 mm, or another intermediate margin of error.

In some embodiments of the invention, several sets of measurements x are obtained in X; each set x being made up of a plurality of measurements $x_i$, $x_j$, ... from different sensor (e.g., electrode) positions i, j, ... with distances between at least some of the positions being known, so that the distances can be used as a constraint.

In some embodiments, the measurements are known to be obtained by sensors fixed at known distances from one another, e.g., because they were obtained from a plurality of different sensors positioned at fixed distances on an intrabody probe. However, the known relative position constraint is not limited to the use of sensors arranged in a linear, ruler-like configuration. For example, in some embodiments, the sensors are arranged in pairs, where each two electrodes in a pair are so close that the catheter cannot practically fold between them, but the inter-pair distances are large enough so that the catheter may fold between pairs. In such an embodiment, intra-pair distances may be known, and inter-pair distances may be unknown. It has been found that the intra-pair distances may be sufficient for obtaining useful approximations. The mutual constraint optionally comprises another constraint based on distance and/or relative angle of measurements. More formally, for example, the measurements are position-constrained such that a transform yielding distance $|T(x_i)-T(x_j)|=\Delta Y'_{ij}$ can be found, with a result that is potentially a good approximation of the actual distance. Optionally, the transform is found by a process of "energy" or error reduction as just outlined.

Considering local spatial calibration (e.g., MDS-used) constraints alone, the relative positions of each separate set of measurements (e.g., a set of measurements taken at different times and/or at different locations in the target) are unlinked. Therefore, there may remain uncertainty about how different measurement sets should be related to one another in space.

In some embodiments, this problem is alleviated at least in part by assumptions about coherence between distances in the measurement space and distances in the physical space. Optionally, the requirements for coherence and for local spatial calibration are weighted relative to each other to achieve reduced reconstruction error.

Conceptually, the weighting can be thought of as allowing mutual position constraints to act as a ruler, measuring differences between positions in units of distances between electrodes, and influencing and/or partially overriding the local conditions of coherence. Conversely, the constraint of coherence may help to assign different sets of measurements to positions in space, while mitigating distorting effects of measurement noise. As more measurements are made, the limits of the body cavity in which the probe is moving will limit the extent of movements, so that the reconstruction Y' potentially grows to more closely resemble the actual shape of the cavity Y.

In some embodiments, for example, the transform T is defined as a transform that minimizes a suitably weighted joint error in satisfying both the coherence condition and local spatial constraints. For example, error with respect to local spatial constraints is optionally found from $|T(x_i)-T(x_j)|=\Delta Y'_{ij} \approx \Delta Y_{ij}$, where the error is in the deviation of distances in Y' from known real-world distances in Y (e.g., error is |Y'-Y|, or another suitable error metric). Similarly, error with respect to coherence is optionally found from $\Delta X \propto \Delta Y'' \approx \Delta Y'$, where the error is in the differences in Y' from the coherence-modeled output Y'' (e.g., error is |Y'-Y''|, or another suitable error metric). Minimization of error is by any suitable technique, for example, statistical analysis and/or gradient descent. The symbol ≈ is used herein to show that discrepancies between the terms on its both sides (in this case, between T(x) and Y), are minimized by use of a suitable reconstruction procedure, although equality cannot be guaranteed.

In some embodiments, a reconstruction of Y is produced exclusively or almost exclusively based on sensor measurements, their known distances, and the assumed coherence model.

In some embodiments, a reconstruction of Y is produced exclusively or almost exclusively based on imposing local spatial position constraints and coherence constraints on a set of measurements.

Optionally, a few further conditions are set to guide the reconstruction process—for example, broad assumptions about the orientation and voltage ranges of electromagnetic fields being measured, positions of landmarks, and/or global constraints on positions and/or orientations which the intrabody probe can physically reach based on its size, flexibility, entry point to a chamber, etc. In some embodiments detailed initial conditions are set for the reconstruction.

In some embodiments, a coherent transformation may be obtained by a spectrum decomposition method, for example, by a diffusion map algorithm. In some embodiments, such a transformation may be segmentation preserving. Some such embodiments are described below using the concept of displacement.

The displacement concept can be understood if the voltage points V are envisaged first to be "copied" to initial location points Y, e.g., by a transformation Y=aV, where a is a constant, and has units of distance/measurement (e.g., mm/mV). Then the initial location points aV are displaced by a displacement W to have the proper local scaling (i.e., to keep the sister distance constant). In some embodiments, in addition to the local scaling, a coherence constraint is applied. The coherence constraint may be that W is smooth, so if it is decomposed to components of different spatial frequencies (e.g., to Fourier components), it has only components of low spatial frequencies.

Each constraint may be embodied by applying a penalty to a transform insofar as the transform violates the constraint. For example, the constraint to have the sister distances as accurate to their known distance as possible, may be embodied in a "penalty" applied to transformations that generate sister distances that deviate from the known "ruler" length: the larger the deviation—the larger the penalty. Thus, adjusting the transform to reduce the penalty applies a criterion for reducing the variability in the sister distances. In some embodiments, reducing variability in sister distances reduces differences between distances of sister locations and the known distance. In some embodiments, an attempt to have the sister distance as similar as possible to the known distance will be in addition to a requirement that the sister distance will be kept as constant as possible across the reconstruction. In some embodiments, a constraint to minimize differences between sister distances and the known distance may result with reduced variability of the sister distances without posing an explicit constraint on the variability.

The constraint to have the displacement change smoothly, in a coherent manner, may be achieved by applying a "penalty" to the various components of the displacement: the higher the spatial frequency of a component, the larger is the penalty to its contribution. Once a displacement W that minimizes the overall penalty (e.g., a sum, optionally a weighted sum, of the penalty for sister distance variability and the penalty for high spatial frequencies) is obtained, it may be used to displace the initial locations to their new locations, which represent a reconstruction of the body-part.

Finding W that minimizes the penalty may be carried out using standard minimization procedures.

In some embodiments, coherence is defined by terms of natural distances. In some such embodiments, the displacement W is expressed as a multiplication of two matrices: W=UW', with U being a representation of V in coordinate system "natural" to V, and W' being the displacement at the same "natural" coordinate system. One example of a "natural" coordinate system of V is a coordinate system where the axes are characteristic vectors (a/k/a eigenvectors) of a normalized kernel of V.

For example, the kernel may be defined as $$K(x, y) = e^{\frac{-\|x-y\|^2}{\sigma^2}}$$

normalized by $$S = \sum_j k_{i,j}$$

so that the normalized kernel is K/S and decomposed by the Graph Laplacian.

In some embodiments, not all the eigenvectors are used, but only those of the smallest frequencies, i.e., associated with the largest eigenvalues (or with the smallest eigenvalues, depending on how the kernel was normalized). Eigenvectors of high frequency are typically more influenced by noise in the measurement cloud, then by major structural characteristics of the cloud. Thus, taking into account only the eigenvectors associated with the lowest frequencies allows grasping the major structure of the cloud while cleaning part of the noise, and ensures that the displacement UW' would be of at least some smoothness. Furthermore, giving up the eigenvectors of the highest frequencies reduces the dimensionality of the problem, as the displacement W' is limited to displacements along the low frequency eigenvectors (and linear combinations thereof). This may be somewhat equivalent to defining in the cloud some sub-clouds (which may also be referred to as segments) that together reproduce the major structural characteristics of the cloud, and limit the displacements to be within these sub-clouds. Therefore, this method may be considered segmentation preserving.

In some embodiments, the coherence criterion is also implied using the intrinsic geometry of the V-cloud. This may be achieved, for example, by defining the smoothness criterion (which gets a larger penalty the larger it is) as $W^T \Lambda$, where $\Lambda$ is a diagonal matrix of the eigenvalues that correspond to the eigenvectors making up U.

Additional Constraints on Reconstruction

An aspect of some embodiments of the present invention relates to the use of additional constraints to create a body cavity reconstruction based on constraints of coherence and local spatial position, e.g., the geometrical configuration of sensors on an intrabody probe. Optionally, the additional constraints are based on additional information to that used to shape or constrain the reconstruction just described.

Anatomical Data

In some embodiments, the additional information comprises known anatomical data. Optionally, the anatomical data is fairly detailed and particular to the patient. For example, the anatomical data may be obtained directly from the patient, such as from segmentations of MRI or CT data, and/or from a reconstruction using other data, for example, a previous reconstruction created based on mapping of electrical measurements. Optionally, the anatomical data are less particularly matched to the patient, e.g., obtained from atlas data (e.g., matched to patient age, gender, weight, etc.). Optionally, the anatomical data is partial; for example, comprising specifications of relative distances between anatomical landmarks to which a reconstruction is scaled. For example, the reconstruction may be constrained so that separately known distances between anatomical landmarks, known independently of the measurements, are consistent with distances assigned between V cloud measurements taken at the anatomical landmarks, and the known distances between the sensors. Moreover, the separately known distances between the landmark positions, combined with measurements taken by sensors at the anatomical landmarks, may provide data on the measurement gradient (e.g., in mV/mm) at the landmarks. Measurement differences between the landmarks (e.g., in mV) may then be divided by the gradient to obtain a physical distance between the landmarks (e.g., in mm). In some embodiments, such physical distance is constrained to be in accord with the additional information available for the reconstruction process.

Such additional information can be obtained from CT data, MRI data, atlas data, previous reconstructions, or any other suitable source. In some embodiments, the anatomical data, e.g., an anatomical image or data of a body cavity, may be used for imposing similarity constraints on the reconstruction, e.g., such that the reconstructed body part may be similar to what is expected from the anatomical data Y, for example: transform T(x) may be calculated such that T(x) ≈Y, where Y is based on the anatomical data.

Optionally, this transformation is used as an initial state at the beginning of a procedure, and replaced and/or refined as more position data become available.

In some embodiments, landmarks are identified by constraints on movement of the probe itself. For example, a wall of a cavity may be identified at a region never crossed by the probe. In some embodiments, landmarks are identified based on characteristic dielectric and/or electrical conduction properties in the vicinity of the landmark.

In some embodiments, maps of how the measurement values are expected to distribute in space (at least approximately) are used as constraints. For use in navigation, this can be based, for example, on simulations of electromagnetic field voltages in space, based on considerations of electrode configurations and/or body tissue dielectric properties.

Auxiliary Fields

An aspect of some embodiments of the present invention relates to the use of auxiliary fields to reconstruct a body cavity based on the constraints of coherence and the geometrical configuration of sensors on an intrabody probe.

In some embodiments of the invention, three electromagnetic fields may be sufficient for the reconstruction, but more may be used. The three electromagnetic fields may be generated by (transmitted from) body surface electrodes configured to establish three crossed, time-varying electrical fields, such that there is some significant component of voltage change in each cardinal direction (X, Y, and Z). Where separate pairs of opposed body surface electrodes are used for each axis (e.g., members of each pair connected in a common circuit, this optionally comprises a six-electrode configuration). In some embodiments of the invention, electromagnetic fields are also generated (transmitted) between non-opposed body surface electrodes, in any suitable combination (pairwise, and/or between groups of electrodes). In some embodiments, supplementary electromagnetic fields generated between body surface electrodes in addition to the first three, are also used for the reconstruction. These "supplementary" fields are not necessarily optimal for primary use in intrabody probe navigation; for example, because their gradients are not very linear in a region of interest, and/or because they are not oriented to provide steep gradients in the region of interest. However, taken as a set of supplementary fields, they provide a source of spatially-ordered sensing data which is used, in some embodiments of the invention, to help in constraining the reconstruction and/or improving accuracy.

Periodically Varying Data

An aspect of some embodiments of the present disclosure relates to the use of periodically-varying data to constrain a transformation of measurements into a reconstruction of a body cavity.

In some embodiments, measurements in X potentially fail to be uniquely mappable to positions in a body cavity reconstruction Y' due to changes in tissue structure over time. For example, the shape of the heart, as well as shapes of various chambers of the heart, are changed during respiration, and, naturally, also during a heartbeat. For example, human heart typically beats between 1 and 2 times a second, and if data is collected at a rate of 100 times per second, data are collected from about 50 to 100 different phases of the heart. Collecting data when the body cavity is at different shapes might affect the reconstruction undesirably. For example, the variation of heart shape during a heartbeat might cause a small location inside the heart to be smeared over a larger portion of the reconstruction. In some embodiments, periodically varying data indicative of the periodical variation in the body cavity shape are collected at the same time the crossed electromagnetic fields are measured. This data may contain, for example, heartbeat rate, ECG signals, etc. In some embodiments, this periodically-varying data is used to reduce the effect of the periodic change in the body cavity shape on the reconstruction of the body cavity.

For example, movements of tissue due to respiration and/or heartbeat can change the shape of the voltage distribution of electromagnetic fields in a heart chamber, so that a probe which is fixed in position still measures phasic voltage changes. In some embodiments of the present disclosure, a transform from measurement space to physical space is defined to be dependent not only on the measurements of the electromagnetic fields X, but also on one or more periodically varying variables, also referred to herein as phasic variables. For example, T optionally depends on the state of phasic variables θ for respiration phase, and/or φ for heartbeat phase to yield T(X,φ,θ)=Y'. Optionally the transform result Y' is phase-stabilized so that it approximates a static cavity shape Y (e.g., a "snapshot" of a heart cavity at some particular phase of the heartbeat cycle and/or the respiratory cycle). Optionally, Y' is dynamic, approximating a phase-dynamic cavity shape Y(φ,θ). Optionally, there is a combination of phase-stabilization and phase-dynamism; for example, stabilization/dynamism with respect to selected reconstructed areas and/or with respect to particular time-dependent processes.

In some embodiments of the invention, data allowing phase-independent identification of reconstruction regions is obtained by pressing an intrabody probe against a moving tissue region to essentially immobilize the tissue relative to the probe. Measurements measured under this condition, referred to herein as "static measurements", may change over time mainly as a function of the phasic changes. Minimizing the effect of periodic changes in the body cavity shape on the transform may "clean" the transform from the effect of the periodic changes, and bring about a static reconstruction that is less smeared than would be obtained without such minimization. Thus, in some embodiments, a transform may be generated under a constraint that a measurement cloud collected when the probe was immobilized in relation to the tissue, would be transformed to a location cloud of minimal radius in the physical space, thus minimizing the effect of the periodic tissue change on the transform. More generally, the transform may be constrained to minimize the volume in physical space to which static measurements are transformed. In some embodiments, such a transform is used to transform measurements taken when the probe is not immobilized, so as to minimize the effect of the periodic shape change on the obtained reconstruction. In some embodiments, the physician controlling the probe may indicate time periods when he believes the probe is immobilized in relation to the tissue, and only data collected during these time periods are used for generating the transform, which is afterwards used to transform data collected at all times.

In some embodiments, phasic motion is taken into account, by allowing a same voltage measurement to be associated with different locations, depending on the phase (e.g. of respiration and/or heart-beat) at which the measurement was made. This may be accomplished by using time varying data indicative of the phase of the body cavity as input, so that the input has more than 3 dimensions, for example, three voltages of the crossing electromagnetic fields, one respiratory phase, and one—heart-beat phase. In such an example, the distance between measurements (e.g., as appears in the above-mentioned kernel) is defined in a 5-dimensional space. In some embodiments, such a definition of the kernel allows transforming differently data collected at different phases, and providing a reconstruction where the effect of the phasic motion is minimized.

It should be noted that the fixed-position technique also potentially makes measurements at both a contacting electrode (in direct contact with tissue), and at non-contacting electrodes (spaced from the tissue). Fully out-of-contact measurement sets can potentially be incorporated into the reconstruction based on similarities to measurements made while contact was at a fixed tissue region of reference, potentially helping to propagate phase-influenced information into regions more distant from body cavity walls at which the fixed-position technique can be applied. In particular, phase-influenced measurements during free movements of a probe potentially mix movement of the probe itself (e.g., due to being jostled at an anchoring position), with changes to the environment. Some degree of statistical separation between movement of the probe and of movement of nearby tissue is optionally obtained by comparing immobilized and non-immobilized measurement readings from nearby positions.

In some embodiments, non-repeating time-dependent changes in tissue state are accounted for by a transform. For example, there may be changes to the voltage gradient of an electromagnetic field due to changes in overall tissue thickness and/or chamber size during a procedure. This can be due, for example, to changes in patient hydration, and/or to changes in edema state of tissue surrounding the body cavity (e.g., triggered by ablation). Changes in heart rate can also potentially cause changes in tissue thickness/heart chamber size, as a faster heart rate results in less relaxation of tissue between beats. Optionally, these effects are measured, for example, by use of periodic spot-checks to determine the thickness of reference regions of tissue, information which is optionally used to update the reconstruction. In some embodiments, modeling is used (e.g., modeling of chamber size/tissue thickness as a function of heart rate) to make suitable adjustments to the transform. Again, the transform results Y' are optionally dynamic (e.g., showing time-dependent changes), stabilized (e.g., suppressing changes by accounting for their effects), or any suitable combination of the two.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Methods and Systems for Tissue Reconstruction from Intrabody Probe Data

Reference is now made to FIG. 1A, which is a schematic flowchart of a method for reconstructing a body cavity map using an intrabody probe 11 (shown, for example, in FIG. 12), according to some exemplary embodiments of the present disclosure. Further reference is made to FIG. 12, which schematically represents a navigation and treatment system 1 used with a reconstruction service module 21, according to some exemplary embodiments of the present disclosure.

Acquisition of Spatial Position Data From Electric Field Measurements

In some embodiments, a method of acquiring position data comprises inducing at least one time-varying electromagnetic (EM) field 4 (for example, three or more crossing electromagnetic fields, each of a different frequency) generated by an electromagnetic field generator/measurer 10 (which is optionally itself comprised of a plurality of field generation modules) using electrodes such as body surface electrodes 5 across a region of body 2 including a body tissue region 7 that is targeted to be navigated by catheter 9 comprising catheter probe 11. Herein, examples shown with respect to a catheter probe 11 should be understood to be optionally applicable to any navigable intrabody probe 11 suitably configured for obtaining electromagnetic field voltage readings by at least two sensors distanced from each other by a known distance. Typically, the time varying electromagnetic field is induced with a total inter-electrode voltage (body surface-to-body surface) of one volt or less, at a frequency of between about 10 kHz and about 1 MHz.

At block 110, in some embodiments, position data is acquired from an intrabody probe (e.g., catheter probe 11), from each of a plurality (e.g., 2, 3, 4 or more) of sensing electrodes 3 on the probe which act as sensors to measure electromagnetic field data indicative of position.

In some embodiments of the invention, the sensing electrodes 3 are in a known spacing relative to one another; for example, fixed at certain distances from one another. Alternatively, if the sensing electrode 3 spacing is dynamic (e.g. because the probe 11 can bend), the spacing can be estimated to change in correlation with parameters of probe operation (e.g., active deformation) and/or measured contact (e.g., deformation correlated with measurements of contact force). The known spacing is used, in some embodiments, as part of the data used in the reconstruction of the body cavity (e.g., a lumen of a hollow organ such as a heart chamber) within which the intrabody probe moves.

In some embodiments, position data is received by computer circuitry, e.g., from the sensors in real time or from a computer memory that saves data received from the sensors.

Figure 2:
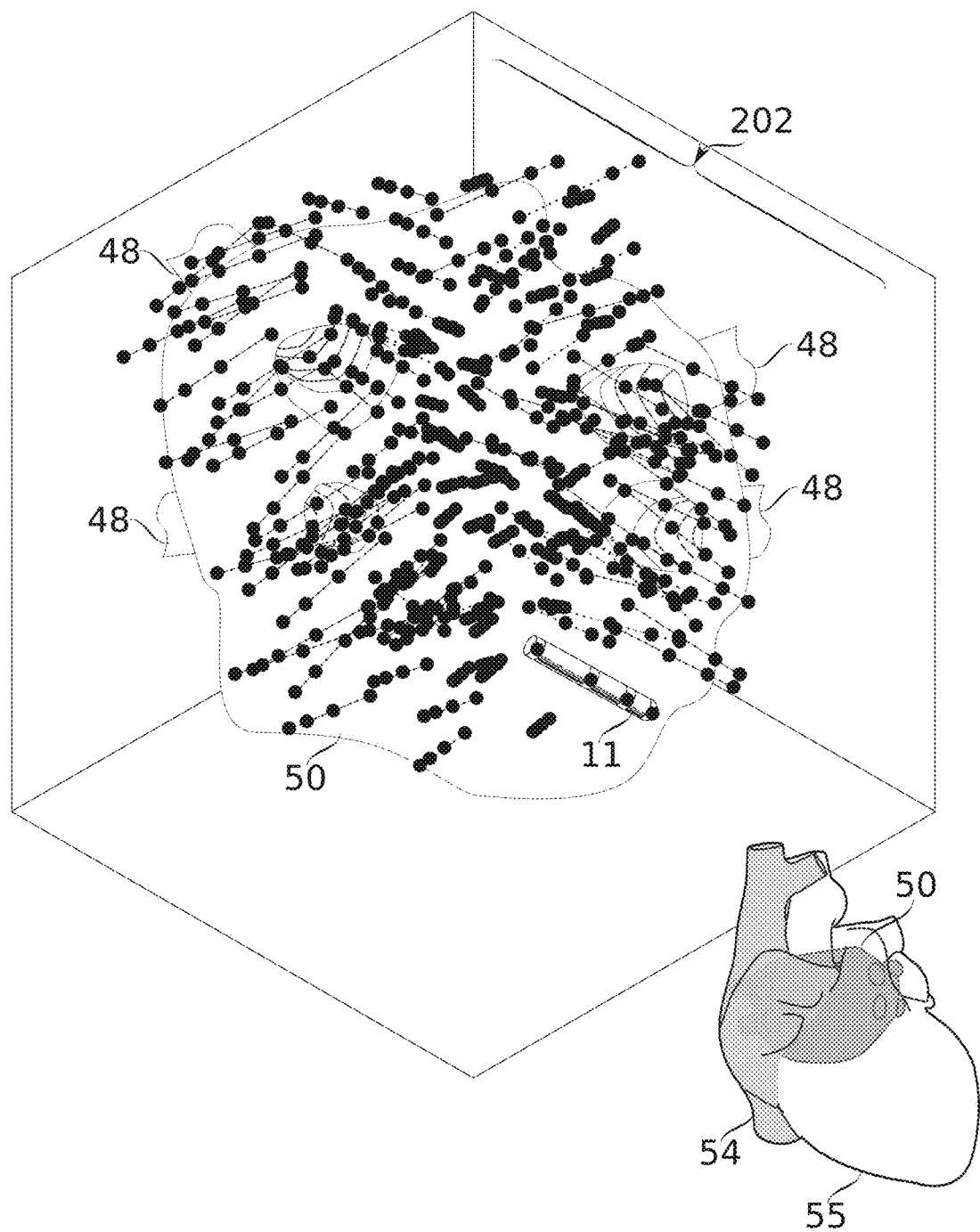
FIG. 2 schematically represents sample positions of a voltage sample cloud shown mapped via a voltage/spatial mapping to a space representing a cavity of a left atrium of a heart.

Before continuing with discussion of elements of FIG. 1A, reference is now made to FIG. 2, which schematically represents a left atrium 50 of a heart 55. The figure shows positions (dots generally marked as 202) in left atrium 50. The dots represent locations at which voltage measurements were taken for reconstructing a shape of left atrium 50. The voltage measurement taken at locations 202 may serve as an example of position data indicative of the positions of locations 202.

A ventral view of a section of the wall of left atrium 50 is shown in the background of locations 202; including roots of four pulmonary veins 48. The semi-transparent heart 55 drawn in ventral view at the lower-right side of FIG. 2 (and in other figures herein) is provided for orientation to the anatomy of the heart. Right heart atrium 54 (semi-transparent light gray region) is visible from the ventral of the heart. As drawn, left atrium 50 is shown as the darkest region, positioned on the far side of heart 55 (in the same orientation as the larger left atrial wall section in the main part of FIG. 2).

The locations 202 are drawn in clusters of four sister positions connected by a dotted line. Each cluster of sister positions represents electrode positions of a four-electrode example of intrabody probe 11 (shown at lower right of LA 50). For purposes of illustration, only some of locations 202 are shown. For live sampling during a procedure, a sampling rate of several samples per second is used. The number of samples per second may be, e.g., at least 10, 25, 50, 100, or an intermediate number of samples per second). Herein, figures showing a straight-line, four-electrode probe with irregular spacing between the electrodes are used for the purpose of providing examples. Optionally, any multi-electrode probe suitable for introduction to the body cavity of interest can be used. One potential advantage of some embodiments of the present invention is that it is suitable for use with a wide variety of intrabody probes which are already commercially available, and may be in widespread use.

In some embodiments, a probe 11 having 2, 3, 4, 5, 6, 7, 8 or more electrodes 3 is used. Measurements taken from the electrodes at substantially the same time optionally include or define a set of measurements from electrodes constrained in their relative positions by a known geometry of their arrangement, or at least by the distance between them. Optionally, well-characterized movements of the probe (bending near a fixed location, axial translations of the catheter, etc.) are used as parameters indicative of bending to help to define known geometrical rearrangements among sets of measurements taken at different times.

The electrode 3 spacing is optionally at any suitable distance, and may be regular or irregular among different pairs of electrodes. In some embodiments, an intrabody probe comprises a rigid section, with electrodes fixed to the rigid section at known (e.g., predetermined and/or measurable) distances from each other. In some embodiments an intrabody probe comprises multiple flexible probe segments (arranged to open to a predetermined and/or measurable spread-out configuration of inter-electrode distances, e.g., in a "basket"-type and/or "umbrella"-type configuration), each bearing a plurality of electrodes in a configuration extending therealong. Potentially, mapping from more and/or more widely distributed electrodes speeds up reconstruction, e.g., allows "snapshot"-type mapping of a cavity in which the probe is deployed.

Additionally or alternatively, in some embodiments, electrodes are positioned on a flexible member which can assume a curved shape (e.g., by its own predisposition to bend, under remote control, and/or in response to contact force); optionally to the extent of forming a circular and/or spiral configuration. A catheter carrying such a probe is sometimes referred to as a "lasso" catheter. In some lasso catheters, the electrodes are arranged in pairs, wherein the distance between electrodes within a pair is small enough to be fixed even when the catheter as a whole curves. Accordingly, some lasso catheters may include 10 electrodes that define 45 electrode pairs, among which 5 pairs are characterized by a fixed inter-electrode distance, and the inter-electrode distances in the other 40 pairs are not fixed. The relative positions of the electrodes on the flexible member are optionally calculated from knowing a control state of the flexible member, and the effect of that control state on the flexible member geometry. Optionally, electrodes of the flexible member transmit electrical signals between each other, and the level of the electrical signal is used to calculate a distance. In some embodiments, a catheter includes one or more pairs of electrodes with known intra-pair distance (i.e., known distance between the members of the pair), and unknown inter-pair distances (i.e. unknown distances between the pairs or between electrodes that belong to different pairs). In some embodiments, only two electrodes with known distance between them is included in the catheter probe. In some embodiments, the distances between some electrodes on the catheter probe are known, and the distances between some electrodes on the same catheter probe is unknown. All these may be used in embodiments of the invention, as one inter-electrode distance is sufficient to provide a "ruler" to be used in the reconstruction as described below in the context of block 112, although a larger number of known distances may yield a better reconstruction. A reconstruction may be identified as better than another if it provides a more useful approximation of the target than the other reconstruction.

In some embodiments, a plurality of probes is used. Optionally, a first probe (a straight probe or a flexible member probe, for example) is used to obtain position data used to reconstruct the target space, and a second probe (e.g., an ablation probe) is guided to one or more selected positions within the target space, based on the reconstruction, and on measurements made by electrodes of the second probe which correlate with measurements assigned to positions based on the position data obtained from the first probe.

Optionally, sensors in the catheter rely on wireless transmission to transmit measurement to be recorded and processed.

Probe Structure-Constrained and Coherence-Constrained Spatial Reconstruction

At block 112, in some embodiments, the known spacing of sensing electrodes 3 is used in voltage/spatial mapping, whereby the body cavity shape is reconstructed from voltage measurements measured by probe electrodes 3.

A major principle of the reconstruction may be understood as using the structure of the intrabody probe as a kind of ruler. As this ruler is moved among multiple locations, it does not change its length. In some embodiments, possible transforms are weighted by the degree to which they keep this length constant. In embodiments where this is the only criterion for choosing a transform, the transform that keeps this length most constant is chosen to be used for the voltage/spatial mapping. Naturally, when distances between more than two electrodes are known, there are more rulers that should be fixed.

For example, in transforming each measurement made by one sensor at one instance to a corresponding location (corresponding to the location of the sensor at the instance), it is desirable that measurements taken by two sensors, spaced from each other by 2 mm (for example), are transformed to two locations, spaced from each other by 2 mm. At least, if the two measurements are transformed to locations 3 mm apart from each other, it is desirable that this distance of 3 mm is the same regardless of where the probe is. The requirement for a fixed length of the ruler may be translated to a requirement of a flexible transformation between measurement gradient and location gradient. For example, the distance between the location assigned to sensor 1 and to sensor 2 is always to be the same, even if the difference in voltages measured by sensor 1 and sensor 2 varies appreciably (for example, by a factor of 10 or more).

In some embodiments, a method of finding a transform that keeps the sister distances (i.e., distances between locations assigned to two positions of a ruler) constant comprises an optimization process. This can be understood as starting with a trial transform, estimating the degree to which rulers lengths change under this transform, and iteratively changing the transform to reduce this degree, until a minimal degree of change of rulers lengths (and/or maximal stability of rulers lengths) is achieved.

In some embodiments, the trial transform is changed iteratively not only to maximize the stability of rulers lengths, but also to satisfy one or more additional constraints in some weighted combination. In terms of the "ruler" concept, the ruler length is allowed to get a little longer or a little shorter in some region (and/or for some particular measurement) if that helps to produce a reconstruction which does a sufficiently better job of maintaining another constraint criterion overall. In algorithmic terms, there is a "cost" to increasing change of the ruler length, and a "cost" to increasing failure to maintain any other criteria; and the result chosen is the one that minimizes the joint cost of each.

One general type of constraint criterion used, in some embodiments, is to maintain the spatial coherence of the reconstruction, for example by one of the methods described in the Overview. The general principle of coherence is that positions nearby in space should also be nearby in their other properties (and the closer in position, the closer in their properties); and in particular, nearby in the values measured in them to produce position data. For example, one kind of coherent transform is a transform that transforms more-similar voltage readings to more-nearby locations, and less-similar voltage readings to locations further away from each other. In some embodiments, distance between measurements is defined according to the natural distance between them. For example, in some embodiments, the voltages of three different electrical fields are measured as indications of position. These measurements may be represented as points in a three-dimensional space. For example, a Cartesian system of axes may be used to present the voltage readings, when a reading of, say, 10 mW at each field (e.g., at each frequency) is represented at a point distanced from each of the axes by 10 mm. This way, measurements collected at many instances (say, 6000 measurements taken during 1 minute at a rate of 100 measurements per second) may be represented as a cloud of measurements, referred to herein as a V-cloud. The shape of the V cloud is very different from the shape of the target, because the fields are not linear as axes in a Cartesian system. Still, the inventors found that by using coherent transforms that keep ruler length constant, the V-cloud may be transformed into an R-cloud that is a useful approximation of the shape of the target. In some embodiments, the usefulness of the approximation may be enhanced by using natural distances between measurements in the V-cloud and between locations in the R-cloud. The natural distance between two points in a cloud may be the shortest path going from one point to the other without going out of the cloud. The use of natural distance was found to make the transforms segmentation preserving, and avoid or decreases merging of protruding shapes into each other.

As mentioned above, in some embodiments, one or more additional sources of information are used as constraints during production of a reconstruction. These additional constraints may also be applied flexibly by assigning them costs, and finding a transform that minimizes the overall cost, considering ruler length stability, transform coherency, and any other constraint. Examples of additional constraints are described, for example in relation to functionality blocks 1102, 1106, 1108, 1110, and 1112 of FIG. 11.

Display of Reconstructed Structure

At block 114, in some embodiments, a current state of the spatially reconstructed structure produced in block 112 is provided for use. In some embodiments, uses of the reconstructed structure include one or more of:

Display and/or navigation: In some embodiments, a state of a procedure underway within the body cavity is shown in a view that includes a model of the reconstruction. A model of the reconstruction may be any representation of the shape of the body cavity based on the R-cloud, for example, a three-dimensional rendering of a mesh that snugly covers the locations that make together the R-cloud. Optionally, the view also includes a model of intrabody probe 11 at a position within the model of the reconstruction. The position of the probe model in relation to the reconstruction model corresponds to the estimated position of the actual probe in relation to the actual target. Data indicating actual movements of the probe are optionally used to model probe motions in the displayed reconstruction model, allowing the display to be used as an aid to navigation. In some embodiments, the displayed view comprises a real-time updated view of a scene maintained by a graphical display engine (e.g., a game engine), for example as described in U.S. Provisional Application Nos. 62/422,705 entitled REAL-TIME DISPLAY OF TISSUE DEFORMATION BY INTERACTIONS WITH AN INTRABODY PROBE; 62/422,708 entitled TISSUE MODEL DYNAMIC VISUAL RENDERING; and 62/422,713, REAL-TIME DISPLAY OF TREATMENT-RELATED TISSUE CHANGES USING VIRTUAL MATERIAL; each filed on Nov. 16, 2016, and the contents of each of which are included herein by reference in their entirety. It is noted, however, that in the above-referenced provisional patent applications, the target was modeled by a CT image, while in accordance with some embodiments of the present invention, the target is modeled by a reconstruction model of the target.

Procedure assessment: In some embodiments, the reconstruction is used, together with records of intrabody probe movements, records of other procedure actions (such as treatment activations), and/or measurements of tissue from locations within the reconstruction, to generate an assessment of the procedure; e.g., an assessment of current procedure status and/or likelihood of procedure success. Optionally, the assessment is generated as the procedure is underway. Such an assessment is of potential use, for example, in making changes to procedure planning. Optionally, the assessment is generated after a procedure, for example, as an estimate of a likelihood of procedure success. Methods of procedure assessment are described with relation to several different types of procedure outcome estimators, for example in U.S. Provisional Application No. 62/422,748 entitled ESTIMATORS FOR ABLATION EFFECTIVENESS; filed on Nov. 16, 2016, the contents of which are included herein by reference in their entirety.

Procedure planning and/or re-planning: In some embodiments, the reconstruction is used, together with records of intrabody probe movements, other procedure actions (such as treatment activations), and/or measurements of tissue from locations within the reconstructed target, to support planning revisions to a procedure. For example, a line of ablation initially planned for a heart chamber on the basis of pre-procedure imaging is optionally revised to match anatomical details discovered by a reconstruction of the heart chamber, based on movement of the intrabody probe during the procedure itself. Optionally, deviations in treatment execution from an original plan (e.g., missed ablation positions and/or unforeseen delays in ablation) are compensated for based on analysis of details revealed in the reconstruction. The analysis may be by the physician carrying out the procedure and provided with a view of the reconstruction model, or by a processor programmed to analyze the reconstruction. In some embodiments, for example if another treatment procedure is found to be necessary at some time after an original procedure is completed, a reconstruction generated during the original procedure is used as a basis for planning the new treatment procedure.

At block 116, in some embodiments, a decision is made whether or not to return to block 110 and continue acquiring probe geometry-constrained voltage measurements. If so, the flowchart cycles back to use data from block 110 to adjust the reconstruction at block 112 and then provide for use another version of the reconstructed structure. This loop optionally continues for as long as a procedure continues. In some embodiments, the loop continues in order to update the position of the probe model in the reconstruction model. In some embodiments, the position of the probe model is updated, but the reconstruction model is not updated. This may be the case, for example, when the reconstruction model is sufficiently detailed, and further updates may yield no significant additional information for the physician. Unnecessary updates may distract the physician's attention (e.g., by causing the view to flicker).

Accounting for Variability in Voltage/Spatial Mappings

When methods according to some embodiments of the present disclosure are carried out, voltage measured at a given point may change over time; for example, due to movement of tissue around the point where the voltage is being measured. Blood, muscle, bone and air have different impedance properties, and as their relative spatial distribution changes around a heart ventricle (or any other body cavity to be reconstructed), so does the spatial distribution of voltages in the heart ventricle. Accordingly, a static point may be reconstructed to appear at different places due to changing conditions, and any structure reconstructed based on the voltage readings may be reconstructed to have a shape distorted to different extents and in different manners due to the changing conditions. The distortions may also be dynamic, that is, be different at different times.

Figure 3A:
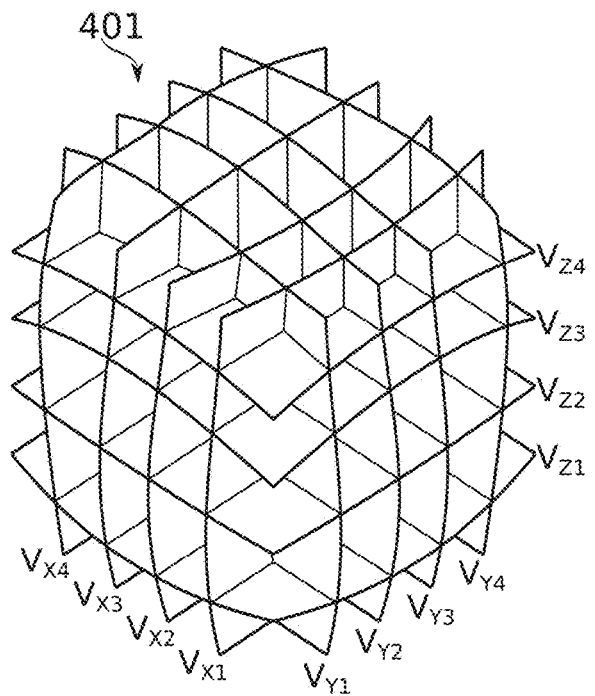
FIGS. 3A-3C schematically represent changes in the spatial distribution of voltages measured within crossing electromagnetic fields as a function of changing conditions such as tissue motion, according to some exemplary embodiments of the present disclosure.
Figure 3B:
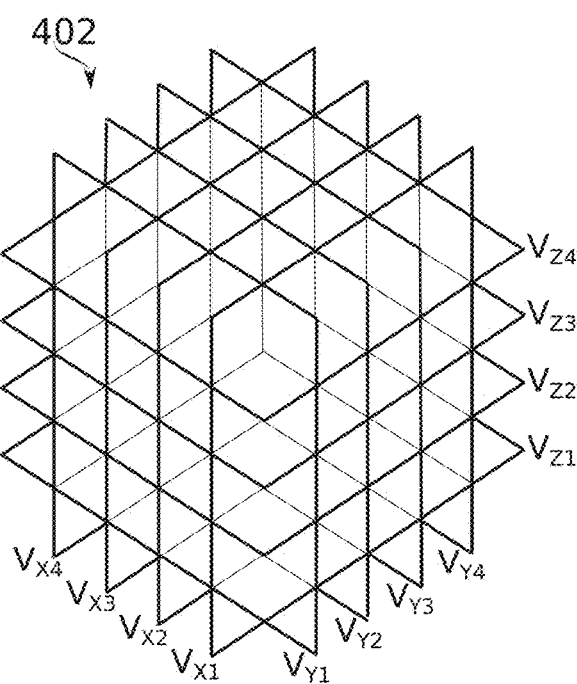
Figure 3C:
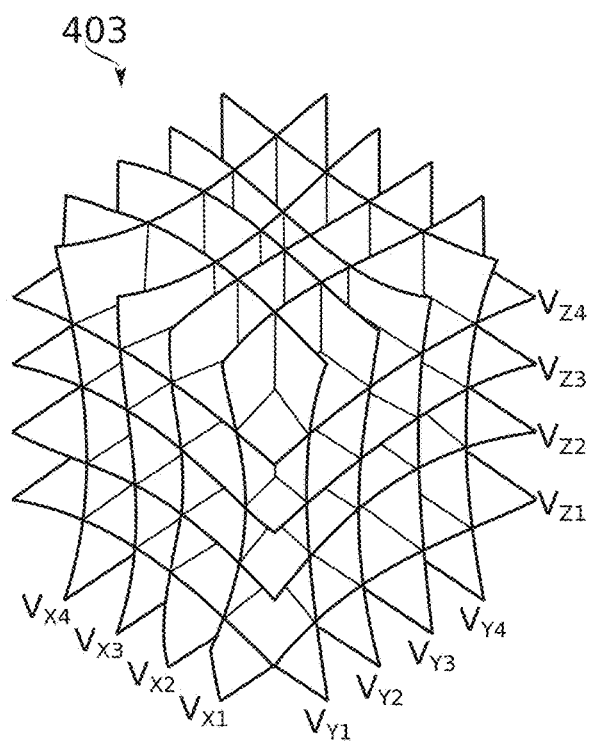

Reference is now made to FIGS. 3A-3C, which schematically represent changes in the spatial distribution of voltages measured within crossing electromagnetic fields under different conditions such as different phases of motion, according to some exemplary embodiments of the present disclosure. For example, each of FIGS. 3A, 3B, and 3C may represent a reconstruction of the same structure (not shown) under different conditions.

Several different types of changes can take place during a procedure which could cause a statically defined voltage/spatial map to fall in and out of registration with reality. Significant among these changes are heartbeat, respiration, and longer-term changes such as changes in hydration state and development of tissue edema.

3-D voltage/spatial mappings 401, 402 and 403 of FIGS. 3A-3C together may represent cyclical change in spatial voltage distribution as a function of a parameter such as heartbeat phase and/or respiratory phase. Iso-voltage surfaces VXn, VYn and VZn represent the same voltage in each mapping, but their positions shift due to changes in the environment around them.

Assuming voltages within a reconstructed structure are distributed on a rectangular grid, similar to that drawn in FIG. 3B, mapping 402 may represent a voltage/spatial mapping at a phase where distortion between the structure and its reconstruction are minimal. At another phase, for example, of heart expansion, the reconstruction may take the form of voltage/spatial mapping 401, which is distended outwardly and non-uniformly. At an opposite phase of heart expansion, the voltage/spatial mapping 403 becomes inwardly collapsed: perhaps non-uniformly as shown.

Such distortion over time is just one example of change. There may also be translation of electric fields as a function of phase, and/or of time.

Figure 5A:
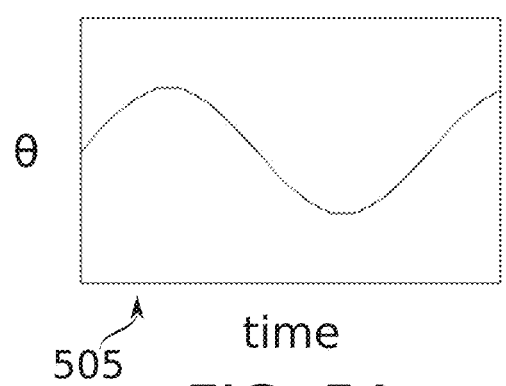
FIGS. 5A-5B schematically represent, respectively, variation over time of a respiration phase θ, and correlated position changes of body tissue, moved during respiration, according to some exemplary embodiments of the present disclosure.
Figure 5E:
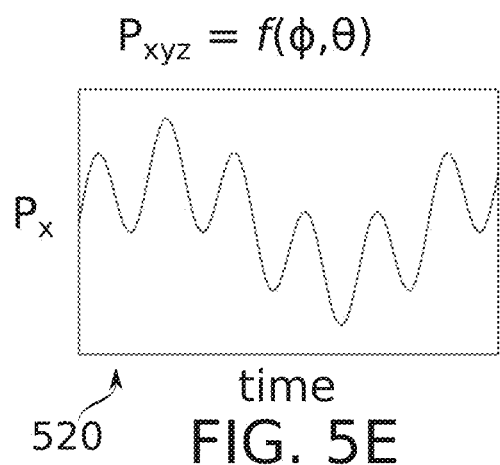
FIG. 5E schematically represents variation over time of a position $P_x$ as a function of both heartbeat phase φ and respiration phase θ, according to some exemplary embodiments of the present disclosure.
Figure 5C:
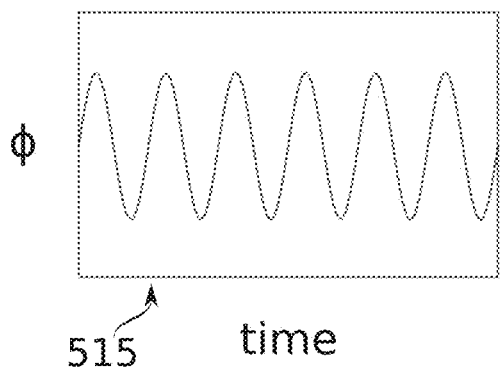
FIGS. 5C-5D schematically represent, respectively, variation over time of a heartbeat phase φ, and correlated position changes of body tissue, moved by the heartbeat, according to some exemplary embodiments of the present disclosure.
Figure 5B:
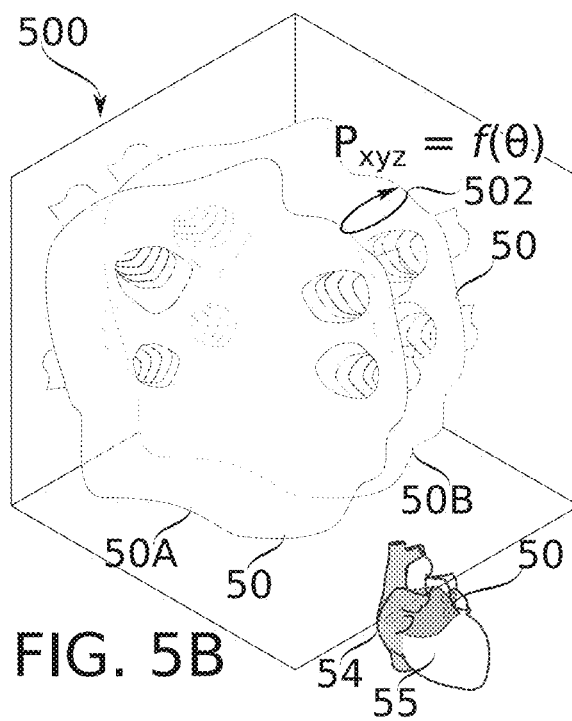
Figure 5D:
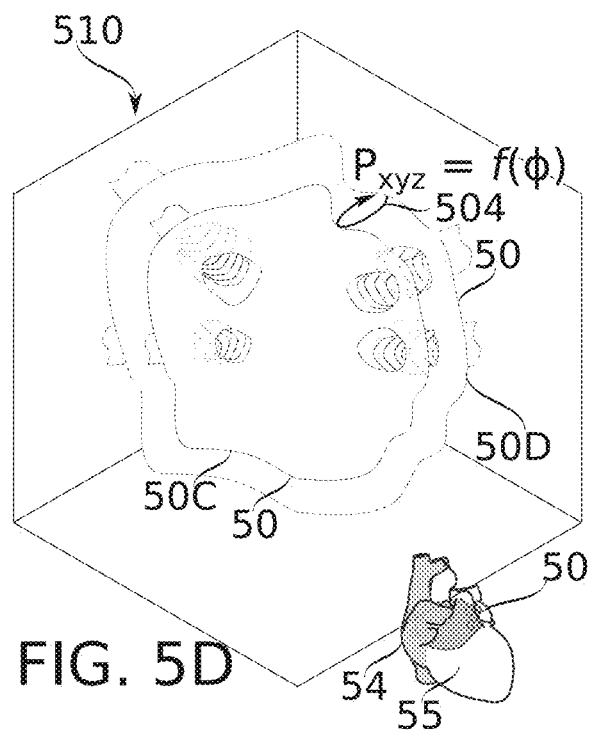

Reference is now made to FIGS. 5A-5B, which schematically represent, respectively, variation over time of a respiration phase $\theta$, and correlated position changes of body tissue 50 moving between positions 50A, 50B during respiration, according to some exemplary embodiments of the present disclosure. Further reference is made to FIGS. 5C-5D, which schematically represent, respectively, variation over time of a heartbeat phase $\phi$, and correlated position changes of body tissue 50 moving between positions 50C, 50D by the heartbeat, according to some exemplary embodiments of the present disclosure. Reference is also now made to FIG. 5E, which schematically represents variation over time of a position Px as a function of both heartbeat phase $\phi$ and respiration phase $\theta$, according to some exemplary embodiments of the present disclosure.

In some embodiments of the current invention, phasic distortion of a voltage/spatial mapping is used to help maintain position accuracy in the mapping as a function of heartbeat phase $\phi$, and/or respiration phase $\theta$. Another way to describe this is that the voltage/spatial mapping is converted to a voltage/spatial/phasic mapping—for example a mapping of voltage V into not only X, Y, and Z spatial axes, but also onto phasic axes $\phi$ and/or $\theta$.

For example, considered ideally, a point P in region 502 of a left atrium in a voltage/spatially mapped space 500 (FIG. 5B) describes a path $P_{xyz}$ as a function of respiration phase $\theta$, which varies over time as shown in graph 505 of FIG. 5A. For purposes of illustration, the path is shown as part of a larger movement of the left atrium 50 comprising a displacement between positions 50A and 50B, but other movements are also possible.

Region 504 of a left atrium in a voltage/spatially mapped space 510 (FIG. 5D) describes another path $P_{xyz}$ as a function of heartbeat phase $\phi$, which varies over time as shown in graph 515 of FIG. 5C (and more quickly than respiration phase $\theta$). Again for purposes of illustration, the path is shown as part of a larger movement of the left atrium 50 comprising periodic contraction and expansion between positions 50C and 50D, but other movements are also possible.

The phase of a heart along a periodic movement (which may be designated above as $\theta$ and/or $\phi$) may be determined, in some embodiments, by measurement. For example, measurement of heartbeat phase optionally uses ECG, oximetry, or pulse meter; and/or measurement of respiratory phase optionally uses a motion sensor, air flow meter, and/or coupling to the operation of a respiratory machine. Optionally, another method of phasic motion measurement is used.

In actuality, since respiration and heartbeat are generally out of phase with one another, the motions experienced by any particular region are subject to more complicated phasic patterns, for example, the phasic pattern of graph 520 of FIG. 5E, which shows a position Px of some region along a single axis as a function of time, where both respiration (varying as $\theta$ in FIG. 5A) and heartbeat (varying as $\phi$ in FIG. 5C) affect position $P_x$.

Figure 12:
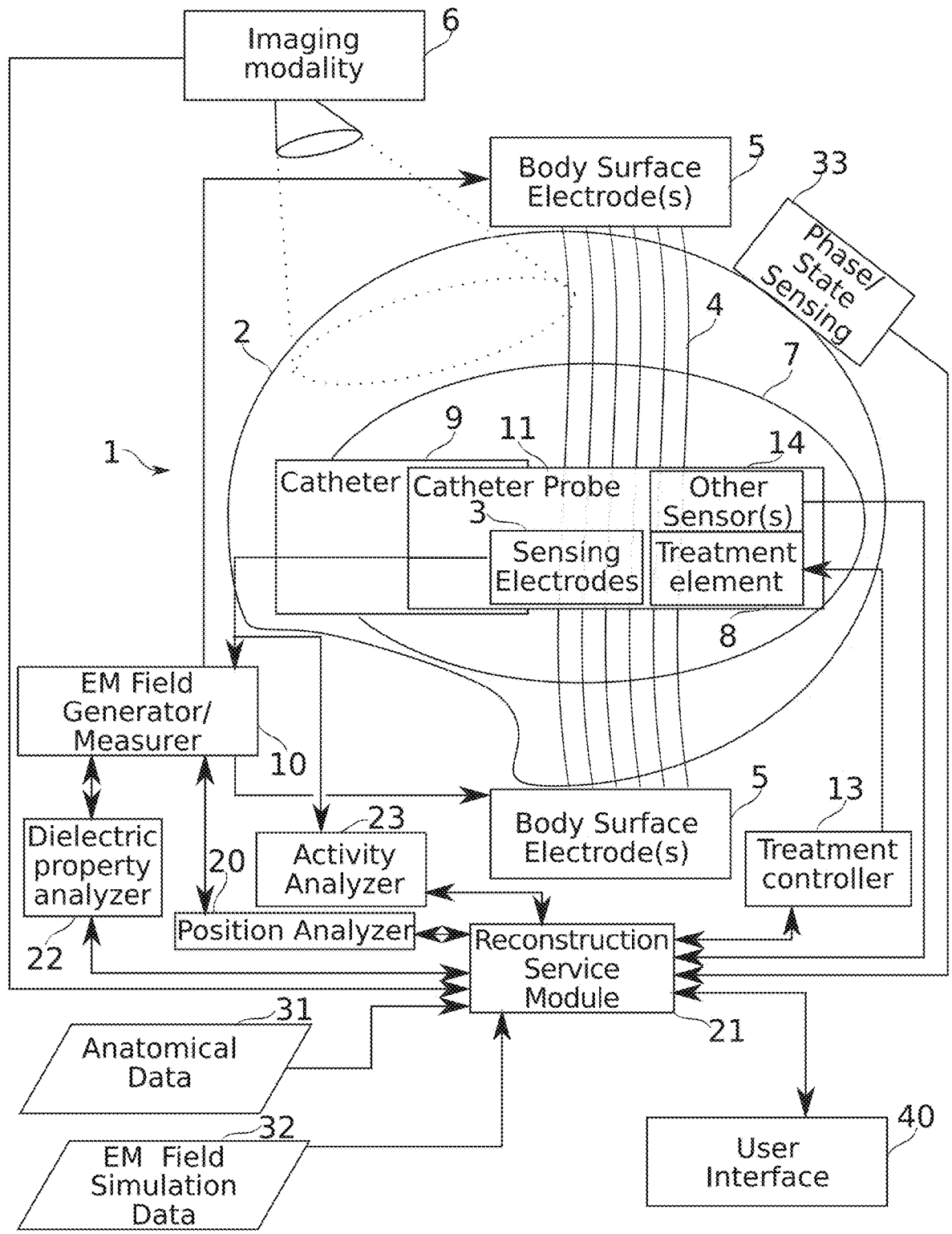
FIG. 12 schematically represents a catheter navigation and treatment system used with a reconstruction service module, according to some exemplary embodiments of the present disclosure.

Given $V_{xyz}=f(\Theta,\Phi)$ for any given region of the voltage/spatial map (i.e., given a voltage/spatial/phasic map), it is a relatively straightforward matter to look up a current position from phase state data provided, for example by means of phase state sensing 33 (FIG. 12).

In some embodiments, the definition of $f(\Theta,\Phi)$ is at least partially based on voltage simulations, imaging, and/or atlas information; e.g., simulations of electrical potential based on how the anatomy is shaped at different phases of respiration and/or heartbeat. Optionally further measurements acquiring voltage measurement data are used to refine a model established by the simulations as a framework (e.g., by weighted combination of simulations and new data).

In some embodiments of the invention, the definition of f(Θ,Φ) is at least partially created by "bootstrapping" from acquired voltage measurement data. For example, a stationary probe experiences phasic differences where it sits. Even for a moving probe, correlation and/or frequency analysis can potentially separate phasic changes at a certain set of frequencies from those due to probe motion.

However, it can be difficult in some parts of a procedure to distinguish phasic motions of the probe (e.g., due to period disturbance by contracting tissue) from phasic changes of the electromagnetic field environment. This is mitigated somewhat, in some embodiments, since the positions of main interest are not usually positions of a probe in fixed space as such. Of more interest, in some embodiments, are positions of the probe relative to—and especially, while in contact with—some particular region of (possibly moving) tissue. The effects of positioning errors occurring while the probe moves freely through a body cavity may be of relatively minor consequence. The effects of positioning errors occurring once the probe is in contact with tissue and providing treatment such as ablation, however, can have less marginal consequences.

In some embodiments of the invention, particular treatment is given to phasic voltage changes occurring while a probe is in contact with tissue. With strong enough contact established (e.g., constant contact even in view of heart contractions), it can be assumed, for example, that the probe is always contacting substantially the same tissue portion throughout all phases of respiration and/or heartbeat. Optionally, contact is measured, for example, using a force sensor (an example of "other sensors" 14 of FIG. 12), and/or by use of voltage measurements which dielectrically and/or by impedance indicate contact (for example, via dielectric property analyzer 22), and/or which indicate electrical activity sensed when tissue is contacted (for example, via activity analyzer 23).

In some embodiments, at each position of such contact, a different "phasic function" is optionally derived. Phasic functions in positions in between measured regions, or for times not measured during contact, are optionally created by interpolation. Even if the phasic function data are incomplete around the whole of a body cavity, it is potentially sufficient to define the result in certain regions of greatest interest, which are often, in some embodiments, the regions where treatment is to be applied.

In some embodiments, phasic and/or other time-dependent changes to the shape of a body cavity are modeled (e.g., simulated) with respect to values of a measurable parameter that indicates the changing shape. Actual measurements of voltage are optionally used to constrain this model, potentially allowing time-dependent measurements from a few locations within the body cavity to be used to set the shape dynamics of the entire body cavity. It should be noted that models of changing body cavity shape and simulations of changing voltages within the cavity are optionally both used.

It should be acknowledged that strong contact between heart and probe potentially itself distorts the phasic data (e.g., the heart is being "held in place" by the probe to some degree, and not beating completely naturally). However, it can be understood that this is actually a potential benefit, in some embodiments where a primary concern is for identification of contacted tissue under conditions where strong contact is required.

While phasic changes to a voltage/spatial mapping are potentially among the most disturbing to accurate positioning, there can also be time-evolving changes that are non-phasic. For example, as a procedure progresses over the course of several minutes (e.g., 30-60 minutes or more), there can be changes in the hydration state of the patient which produce a slowly accumulating error in the voltage/spatial mapping being used. In some embodiments, this error is detected by periodically re-visiting one or more sites, and recalibrating the voltage/spatial mapping on the basis of the sequence of observations made. Optionally or alternatively, hydration state is estimated from exogenous data (e.g., by noting relative fluid flux), and a model adjusted to account for expected differences.

Another source of change, related to heartbeat phase, is that average heart size can change as a function of heart rate. A fast-beating heart relaxes less (e.g., because it has less inter-beat time to relax) than a slow-beating one, so that the faster-beating heart effectively is found to shrink. In some embodiments, this effect is extracted by noting changes in voltage measurements that correlate with heart rate. Optionally, a geometrical model of shrinkage as a function of heart rate is used. In some embodiments, the model is calibrated for a larger heart region based on actual observations of heart size change (or, more directly, voltage change) as a function of heart rate in one or a few smaller regions.

Figure 1B:
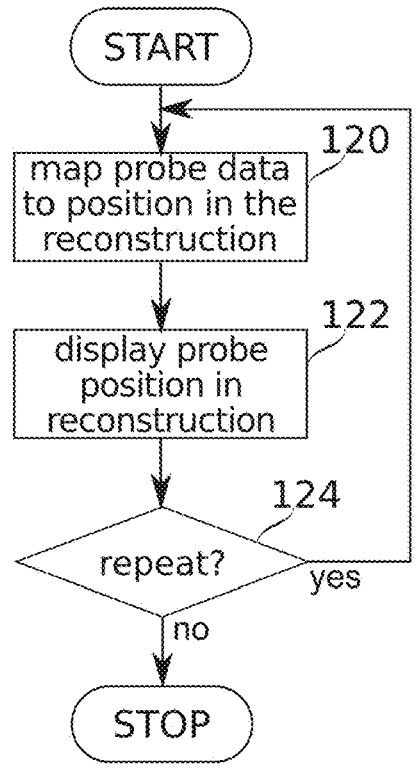
FIG. 1B is a schematic flowchart of a method for using a reconstructed body cavity map together with an intrabody probe, according to some exemplary embodiments of the present disclosure.

Multi-Modality and Multi-Dimensional Mapping
General Use of Intrabody Probe-Acquired Data as Position Data With particular attention to the use of the reconstruction in display and/or navigation, reference is now made to FIG. 1B, which is a schematic flowchart of a method for using a reconstructed body cavity map together with an intrabody probe, according to some exemplary embodiments of the present disclosure.

At block 120, in some embodiments, data acquired from an intrabody probe 11 in some actual body cavity position is mapped to a position in a spatial reconstruction of that body cavity based on a voltage/spatial mapping, for example, a reconstruction as described in relation to block 112 of FIG. 1A.

At block 122, a view comprising an image showing at least a portion of the reconstruction model is shown, together with a model of the intrabody probe 11 at the position to which it was mapped in block 120. A probe may be mapped to a position according to the positions to which electrodes of the probe are mapped. Electrodes may be mapped to a position based on the readings of position-data that they read. For example, when an electrode reads a voltage, the voltage is transformed to a location (e.g., by a transform as described in relation to block 112), and that location is attributed to the electrode. This way, voltage readings by an electrode are interpreted to be indicative of position of the electrode, and position of an electrode may be interpreted as a position of a catheter (or at least catheter portions).

At block 124, a decision is made to continue repeating blocks 120, 122, and 124 (i.e., the procedure of adjusting the position of the probe in the reconstruction model continues) or not (the flowchart of FIG. 1B ends). Optionally, the mapping and display are performed at an image frame rate of at least 10, 15, 20, 30, 60, 100, or another intermediate frame rate. Optionally, the display can be used and interacted with by a probe operator as if it were a direct display of the intrabody probe 11 itself.

The discussions of FIGS. 1A, 2, 3A-3C, and 5A-5E were primarily in terms of electromagnetic field-guided navigation, where a set of crossed, time-varying electromagnetic fields (typically three crossed fields) are used to provide a frame of reference which can be used by means of voltage measurements. However, the data acquired from an intrabody probe 11 can in principle be one of several other possible data types, for example as is now described in the remainder of this section on multi-modality and multi-dimensional mapping.

Multi-Modality Mapping from Probe-Detected Data

Figure 6:
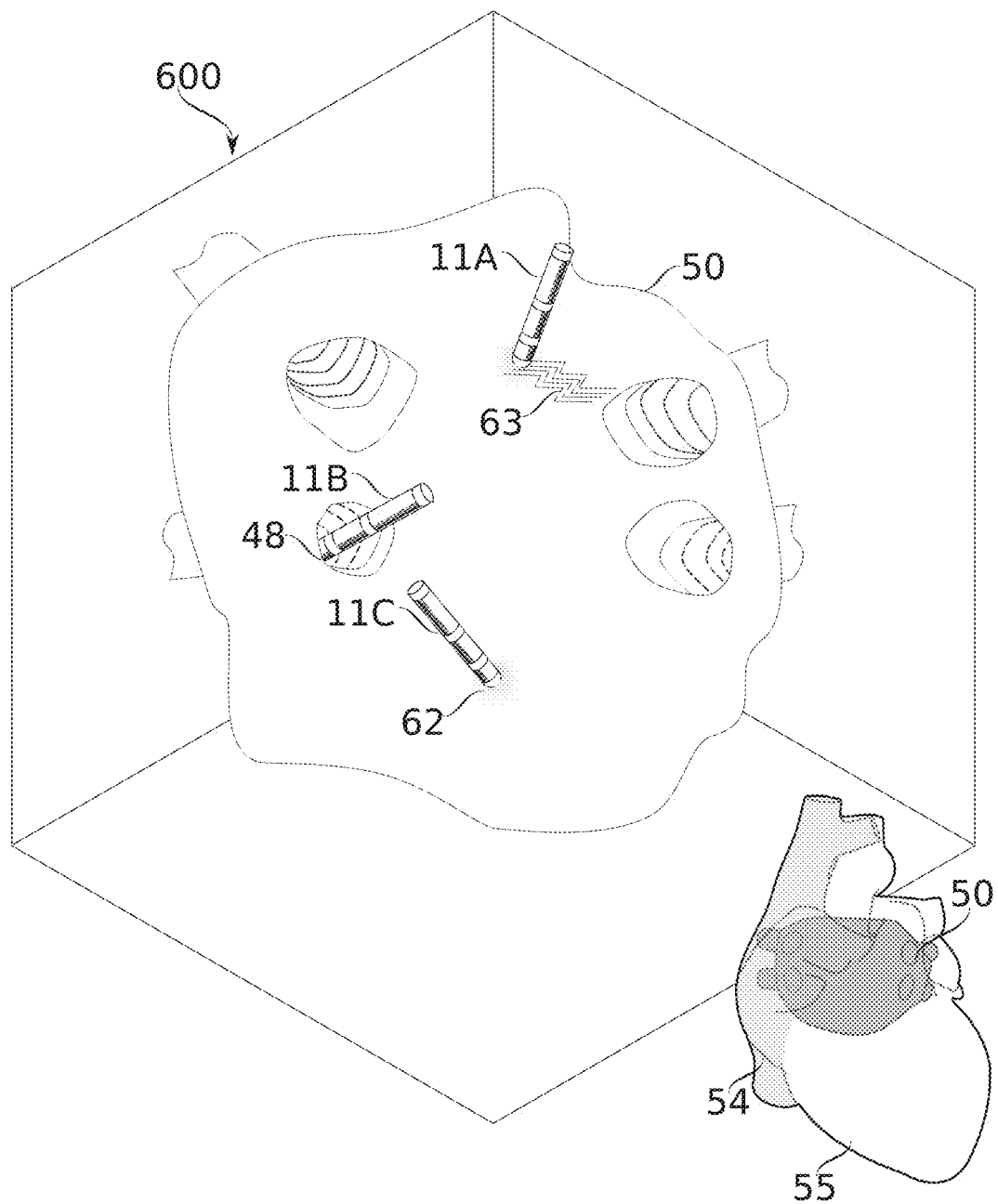
FIG. 6 schematically represents modes of gathering additional position data using an intrabody probe, within a body cavity, according to some exemplary embodiments of the present disclosure.

Reference is now made to FIG. 6, which schematically represents modes of gathering additional position data using intrabody probes 11A, 11B, 11C, within a body cavity, according to some exemplary embodiments of the present disclosure. The probes shown are indicative of different types of data gathering, and do not necessarily imply simultaneous positioning of all the probes.

Probes 11A, 11B, 11C are shown in a space 600 to be mapped, to illustrate acquisition of data from different modalities which can be used to assist in refining and/or using a reconstruction. The different modalities may correspond, in some embodiments, to probe-measured tissue condition sensing data 1105 of FIG. 11. Different types of probe-measured tissue condition sensing are described in relation to each of probes 11A, 11B, 11C.

Probe 11A is shown in the act of measuring endogenous electrical activity 63 in a region of heart atrium wall tissue 50. Optionally, in some embodiments, measured endogenous electrical activity (e.g., an electrogram) is used as an indicator of position, for example, based on a phase delay with which activity is measured at a particular position, compared to some landmark phase, such as the QRS complex of an electrocardiogram (ECG). Optionally, the phase difference is measured relative to an electrode on probe 11A itself, which does not contact the heart atrium wall (also referred to herein as a non-contacting electrode). In some embodiments, the non-contacting electrode may be a ring electrode. Phase-offset correlations between activity measured at the wall and at a non-contacting electrode may potentially help to cancel surrounding noise. This phase delay is optionally treated as creating an additional data dimension applicable across a surface of a heart.

The information gathered this way potentially helps correcting for potential inaccuracies in electromagnetic field-based position data. As an example of such inaccuracies, changes in voltage distribution over time (e.g., as described in relation to FIGS. 5A-5E) could make the same tissue position appear to be slightly different upon a revisit. Registering the electromagnetic field-based position data with electrical activity provides extra information which might prevent unknowingly identifying the revisited (and changed) position with a wrong position, or even help to identify the original position despite its changes.

Probe 11B is shown partially exploring the interior of a root of pulmonary vein 48. Different tissue structures have been found to display noticeably different impedance behaviors which can be gathered by electrodes of an intrabody probe and distinguished through analysis, for example, by a dielectric property analyzer 22 (optionally in communication via electromagnetic field generator/measurer 10 used to operate electrodes 3). In particular, positions within veins and within heart atria are optionally distinguished according to their impedance properties in some embodiments of the present invention, with positions in veins, for example, having the relatively higher impedance value.

In some embodiments, distinguishable dielectric properties of tissue itself can be used as a landmark. Tissue dielectric properties can be measured, for example, as described in International Patent Application No. PCT IB2016/052686 entitled CONTACT QUALITY ASSESSMENT BY DIELECTRIC PROPERTY ANALYSIS, and filed on May 11, 2016, the contents of which are incorporated herein by reference in their entirety.

Impedance changes, for example, due to transitions between two tissue types or between two tissue wall thicknesses, scarring, ablation, edema, and the like) are optionally used as landmarks. Landmarks in turn may be used to register a voltage/spatial mapping to a more accurately determined size. For example, a distance between two landmarks may be known from atlas and/or imaging data; once positions of the two landmarks are known by visiting them and detecting their characteristic properties, the measurements taken at those positions can be constrained to remain at that distance, while other measurement positions are adjusted in between, accordingly.

Additionally or alternatively, such landmarks optionally serve in the re-identification of tissue positions in case of changes to an electromagnetic field-based frame of reference: for example, if an electrode moves, changes its quality of contact, or if a hydration or other state of the patient changes. It is noted that such use of landmarks comprises mapping relative to contact with identified structural features of interest directly, as distinguished from mapping relative to spatially-defined coordinates (at which structural features are supposed to exist). Potentially, this is particularly useful when navigation targets such as in heart atrial wall are in continuous movement relative to spatially-defined coordinates. Optionally, both types of information are used together: for example, a spatial coordinate system is established by measurements of voltages in a spatially distributed electromagnetic fields, and tissue landmarks identified by contact measurements from a probe are assigned coordinates as they are encountered.

Probe 11C is shown in contact with a general region 62 of atrium wall tissue 50 (that is, a region which is not particularly singled out as a landmark). The inventors have found that it is possible, in some embodiments, to detect an anterior-posterior gradient in the size of voltage fluctuations while in contact with atrial heart wall tissue, due to relatively greater anterior movement as a result of heart contraction. Optionally, this fluctuation gradient itself serves as another part of a frame of reference for defining positions in contact with the heart wall.

In some embodiments of the invention, apart from one or more of the various sensing modalities described herein, a position attributed to an intrabody probe 11 (including electrodes 3 thereon) in a spatial frame of reference is constrained by one or more mechanical and/or geometrical considerations (e.g., known shapes of the anatomy constraining motions of the probe). For example, the range of possible positions and/or orientations of a probe known to have entered a region of tissue from a particular entrance point (a vein, artery, or fossa, for example) is optionally restricted to just a plausible subset from all possible positions and/or orientations. Scaling and orientation may also be constrained by such mechanical and/or geometrical considerations. Mechanical constraints on probe shape may also be used in position determinations. Related geometrical and/or mechanical constraints are also discussed herein, for example in relation to FIGS. 10, 1A, and 2.

Other Modalities for Obtaining Voltage/Spatial Mapping Information

Apart from probe-measured sources, other sources of information useful for establishing and/or refining voltage/spatial mapping are available in some embodiments of the invention. It should be understood that these methods of voltage/spatial mapping can optionally be used jointly with the method of FIG. 1A, for example to provide initial maps which are refined by application of the criteria described in relation to block 112, and/or to refine a voltage/spatial mapping provided by the method of FIG. 1A. The combination of techniques can be arranged, for example, by use of a merging algorithm which provides suitable weights to various sources. These sources are now discussed with returning reference to FIG. 12.

To begin with, anatomical data 31 can be sourced from 3-D medical images of the patient, from previously performed mapping-based reconstruction (e.g., using electrical field mapping or another technique such as magnetic mapping or ultrasound mapping) and/or from anatomical atlas data. Optionally, geometrical anatomical landmarks expected from the anatomical data are identified by moving a probe 11 around until it encounters them, and registering voltages to spatial positions according to a characteristic "feature" (such as a wall of a sinus or a cavity of a vein) that is seen in a reconstruction that is formed considering limits imposed on where the probe can travel. Optionally, an overall shape of a voltage-measurement based reconstruction X is subjected to geometrical transformation T to fit the anatomy of a reference geometry Y derived from anatomical data 31. The transformation $T(X) \approx Y$ is optionally described, e.g., by the parameters of an optimal fit of an affine transformation. Additionally or alternatively, in some embodiments, the transformation is based on the mapping of corresponding landmarks in X and Y; i.e. the transformation T is found by matching landmark sets X* (which are subsets of X) in the voltage measurement-based reconstruction with corresponding geometrically located landmarks Y* to find $T(X^*) \approx Y^*$.

Anatomical data can also provide simple constraints to voltage/spatial mapping, for example, by showing in what general region a heart chamber falls compared to the positions of body surface electrodes.

Optionally, anatomical data 31 may be used for constructing more detailed electromagnetic field simulation data 32; for example, as described in International Patent Application No. PCT IB2016/052692, filed May 11, 2016 and entitled FIDUCIAL MARKING FOR IMAGE-ELECTROMAGNETIC FIELD REGISTRATION, the contents of which are incorporated herein by reference in their entirety. The more detailed electromagnetic field simulation data 32 are optionally used to provide a starting point to assign initial positions of intrabody-probe voltage measurements. Alternatively or additionally, the more detailed electromagnetic field simulation data 32 may be used as a post-reconstruction constraint (for example, a criterion which can optionally exclude erroneous measurement values).

Figure 7:
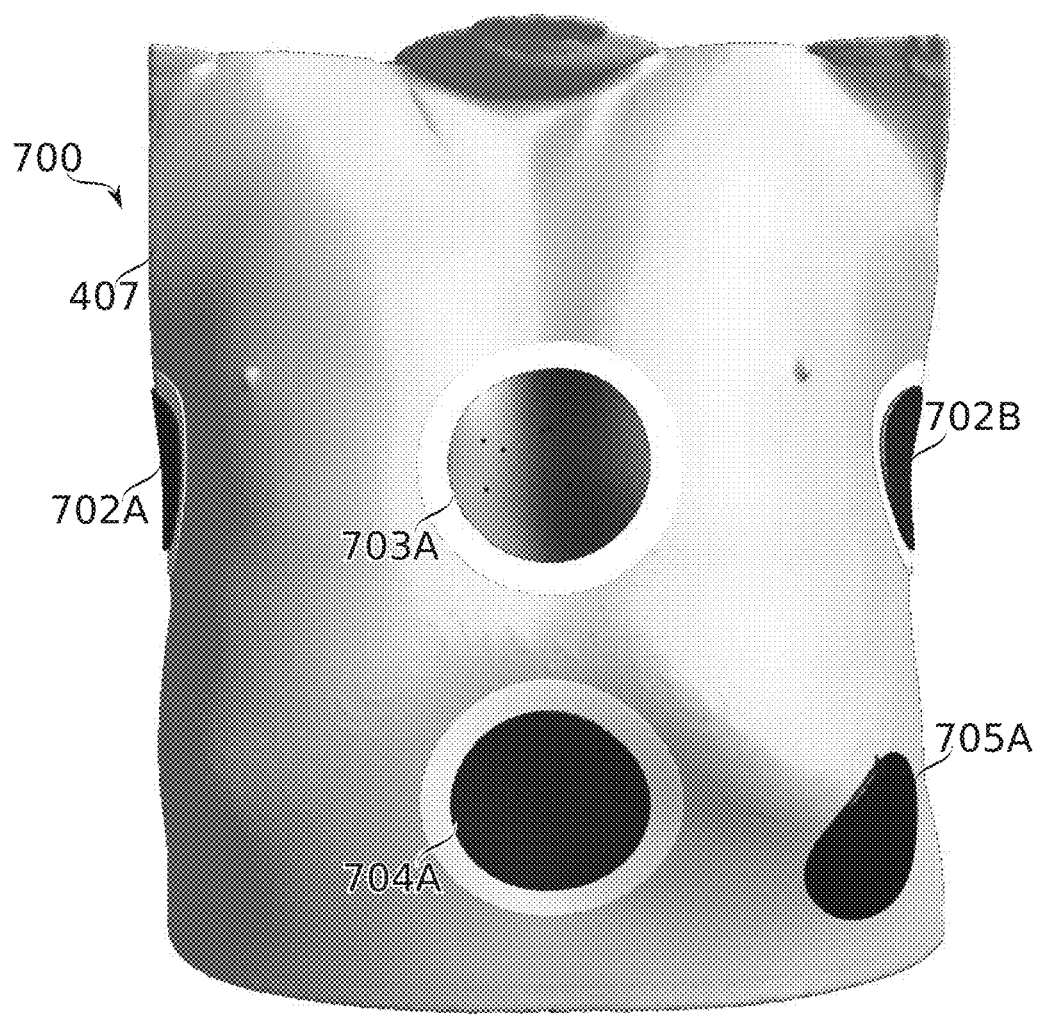
FIG. 7 schematically represents body surface electrodes, positioned on a body for generation of electromagnetic fields used in intrabody mapping and/or navigation, according to some exemplary embodiments of the present disclosure.

Reference is now made to FIG. 7, which schematically represents an electrode configuration 700 comprising body surface electrodes 702A, 702B, 703A, 704A, 705A positioned on a body 407 for generation of electromagnetic fields used in intrabody mapping and/or navigation, according to some exemplary embodiments of the present disclosure. Also, in support of the discussion of figures showing certain anatomical details herein (particularly FIGS. 7-9B 9D), reference is now made to FIG. 4, which schematically represents coordinate systems relative to a human body 407, including an electromagnetic field-defined coordinate system 409 in the region of a heart 55, according to some exemplary embodiments of the present disclosure.

Figure 4:
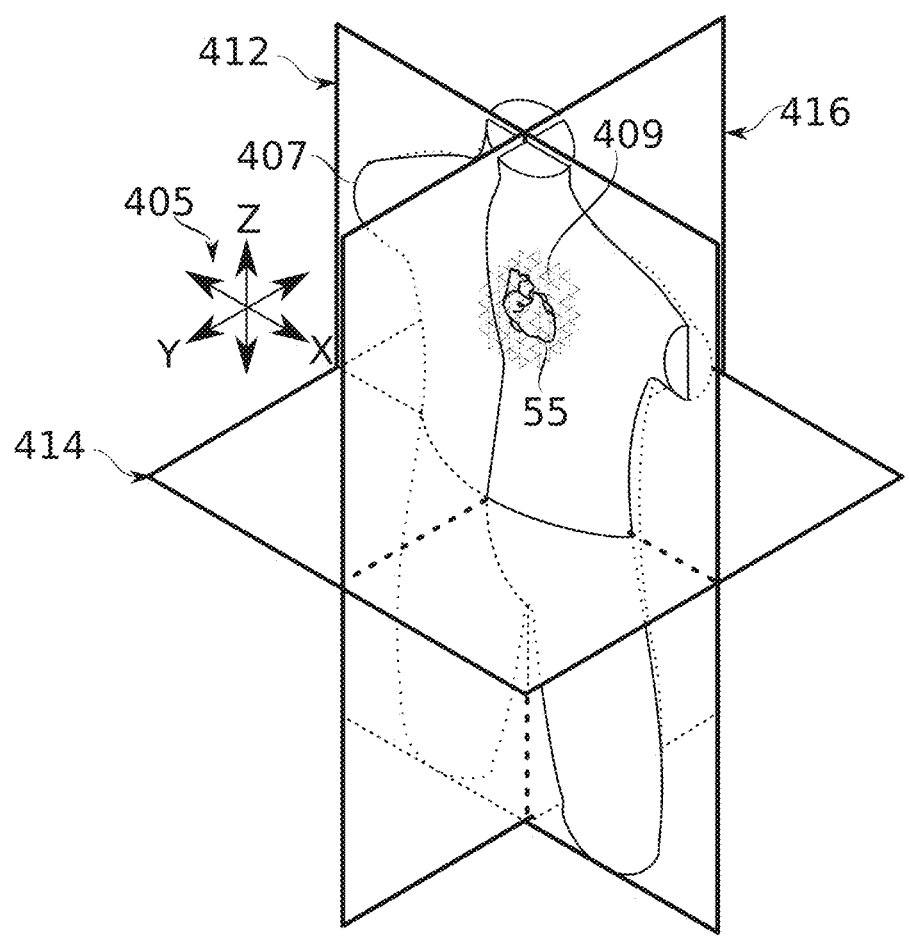
FIG. 4 schematically represents coordinate systems relative to a human body, including an electromagnetic field-defined coordinate system in the region of a heart, according to some exemplary embodiments of the present disclosure.

Shown in FIG. 4 are three cardinal planes 416, 412, and 414: a median plane 416 bisecting a body 407 into left and right portions, a coronal plane 412 bisecting body 407 into ventral (front) and dorsal (back) portions, and a transverse plane 414 bisecting body 407 into top and bottom portions. Axis indicator 405 shows a typical convention used herein for the different anatomical directions—an X axis perpendicular to the median plane, a Y axis perpendicular to the coronal plane, and a Z axis perpendicular to the transverse plane. The co-ordinate system 409 of FIG. 4 may be a "pulsing" coordinate system like that of FIGS. 3A-3C, which provides coordinates for positions within and/or around a body structure of interest during a procedure using an intrabody probe; for example, a heart 55.

Multi-Dimensional Electromagnetic Field Mapping

Figure 8A:
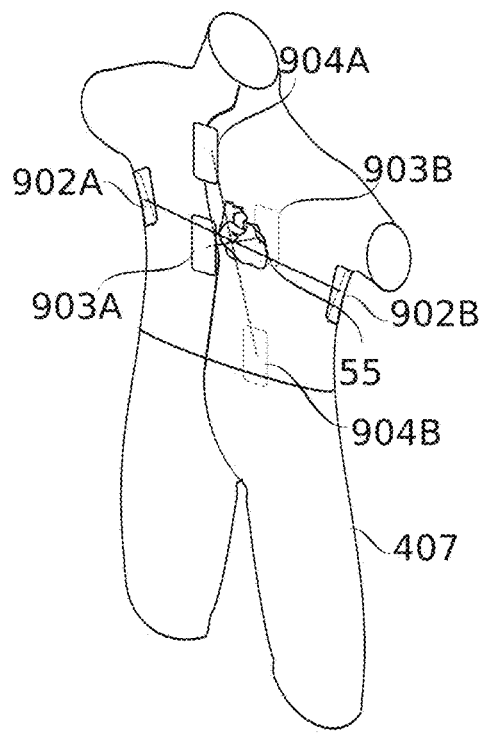
FIGS. 8A-8B schematically represent directions, of principle electromagnetic fields generated by body surface electrodes, according to some exemplary embodiments of the present disclosure.
Figure 8B:
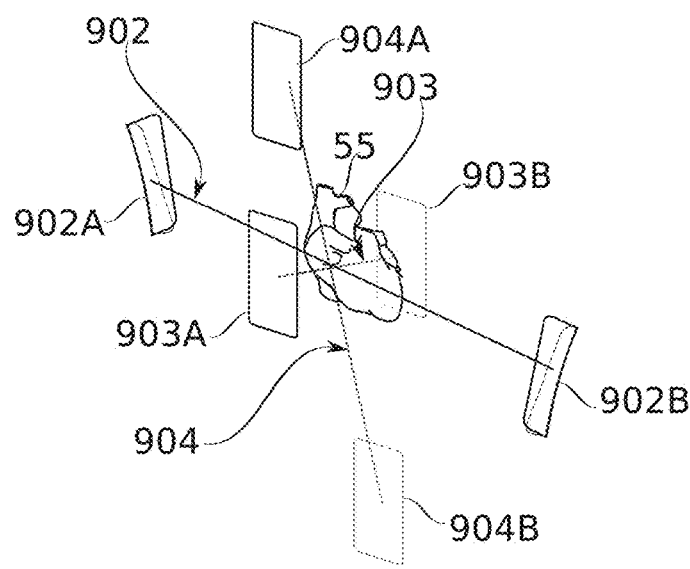
Figure 9A:
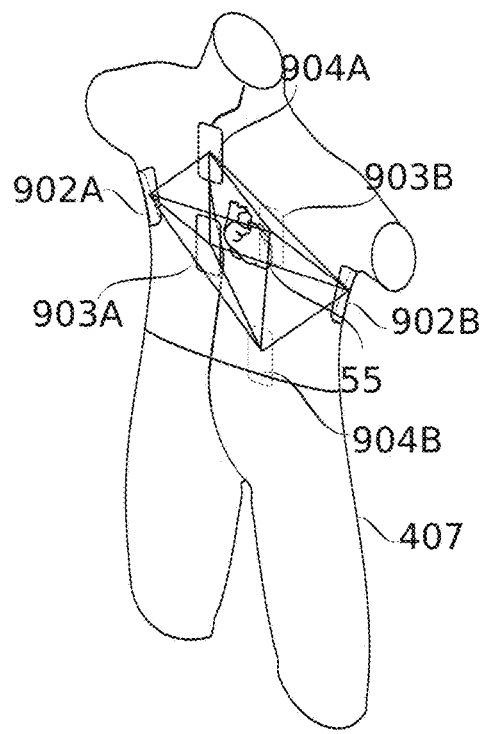
FIGS. 9A-9B schematically represent directions of several auxiliary electromagnetic fields generated by body surface electrodes, according to some exemplary embodiments of the present disclosure.
Figure 9B:
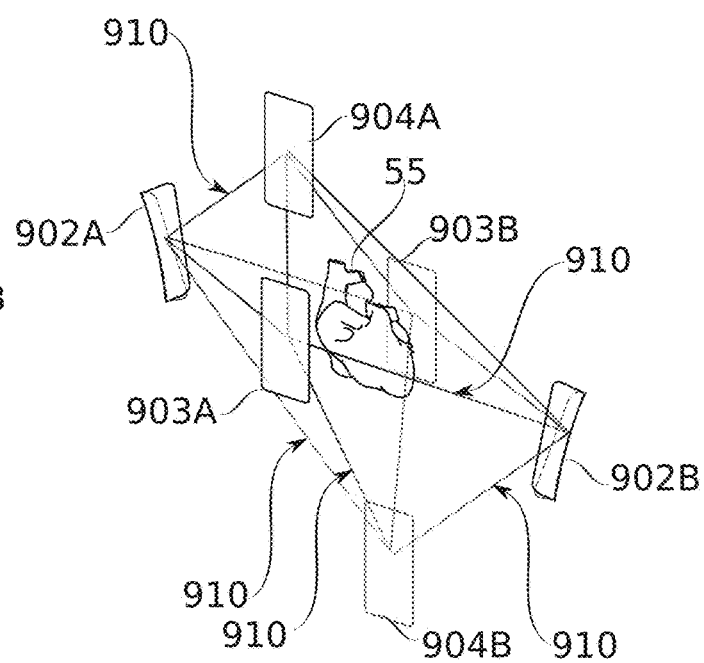

Reference is now made to FIGS. 8A-8B, which schematically represent directions 902, 903, 904 of principle electromagnetic fields generated between body surface electrodes 902A, 902B, 903A, 903B, 904A, 904B, according to some exemplary embodiments of the present disclosure. Reference is also made to FIGS. 9A-9B, which schematically represent directions of several auxiliary electromagnetic fields 910 generated between body surface electrodes 902A, 902B, 903A, 903B, 904A, 904B, according to some exemplary embodiments of the present disclosure.

The body surface electrode and crossed electromagnetic field configuration of FIGS. 8A-8B represents a configuration which may be used for navigation, similar to that of FIG. 7. FIG. 8B is a magnified view of the situation of FIG. 8A, with outlines of body 407 suppressed.

In FIGS. 9A-9B, the same electrode configuration is used, but now including different electrode pairings represented by the directions of auxiliary electromagnetic fields 910. Again, FIG. 9B is a magnified view of the situation of FIG. 9A, with outlines of body 407 suppressed. Optionally, each of these auxiliary pairings is driven at a different time and/or at a different frequency. In some embodiments, analysis of voltage measurements by an intrabody probe (located for example, in the vicinity of heart 55) includes analysis for voltage that varies with respect to position within the various auxiliary electromagnetic fields 910. Each such auxiliary field can thereby supply an additional dimension used in reconstruction, potentially increasing the statistical robustness of reconstruction results.

Dynamic Updating of Reconstruction During Use

Figure 1C:
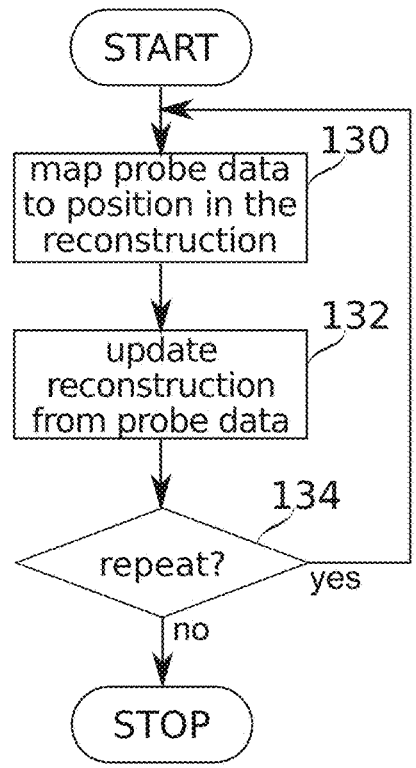
FIG. 1C is a schematic flowchart of a method for updating reconstructed body cavity map based on data from an intrabody probe, according to some exemplary embodiments of the present disclosure.

Reference is now made to FIG. 1C, which is a schematic flowchart of a method for updating reconstructed body cavity map based on data from an intrabody probe, according to some exemplary embodiments of the present disclosure.

At block 130, in some embodiments, position data acquired from an intrabody probe 11 in some actual body cavity position is mapped to a position in a spatial reconstruction of that body cavity based on an existing state of a voltage/spatial mapping, for example, a reconstruction model as described in relation to block 112 of FIG. 1A. The spatial reconstruction of the body cavity at this stage potentially includes sufficient imperfections at the position of the intrabody probe 11 as to require additional refinement before reaching the precision needed for operations of the medical procedure underway.

At block 132, the voltage/spatial mapping is updated, using the position data acquired from the intrabody probe at block 130. In some embodiments, the updated mapping comprises a weighted combination of the new position data, and data previously used in generating the existing state of the voltage/spatial mapping.

At block 134, a decision is made to continue repeating blocks 130, 132, and 134 (i.e., the procedure continues) or not (the procedure ends). Optionally, the mapping and updating are performed at any rate suitable to the rate of data acquisition, for example, at about 0.1 Hz, 0.3 Hz, 1 Hz, 10 Hz, 15 Hz, 20 Hz, 30 Hz, 60 Hz, 100 Hz, or another reconstruction updating rate.

Figure 10:
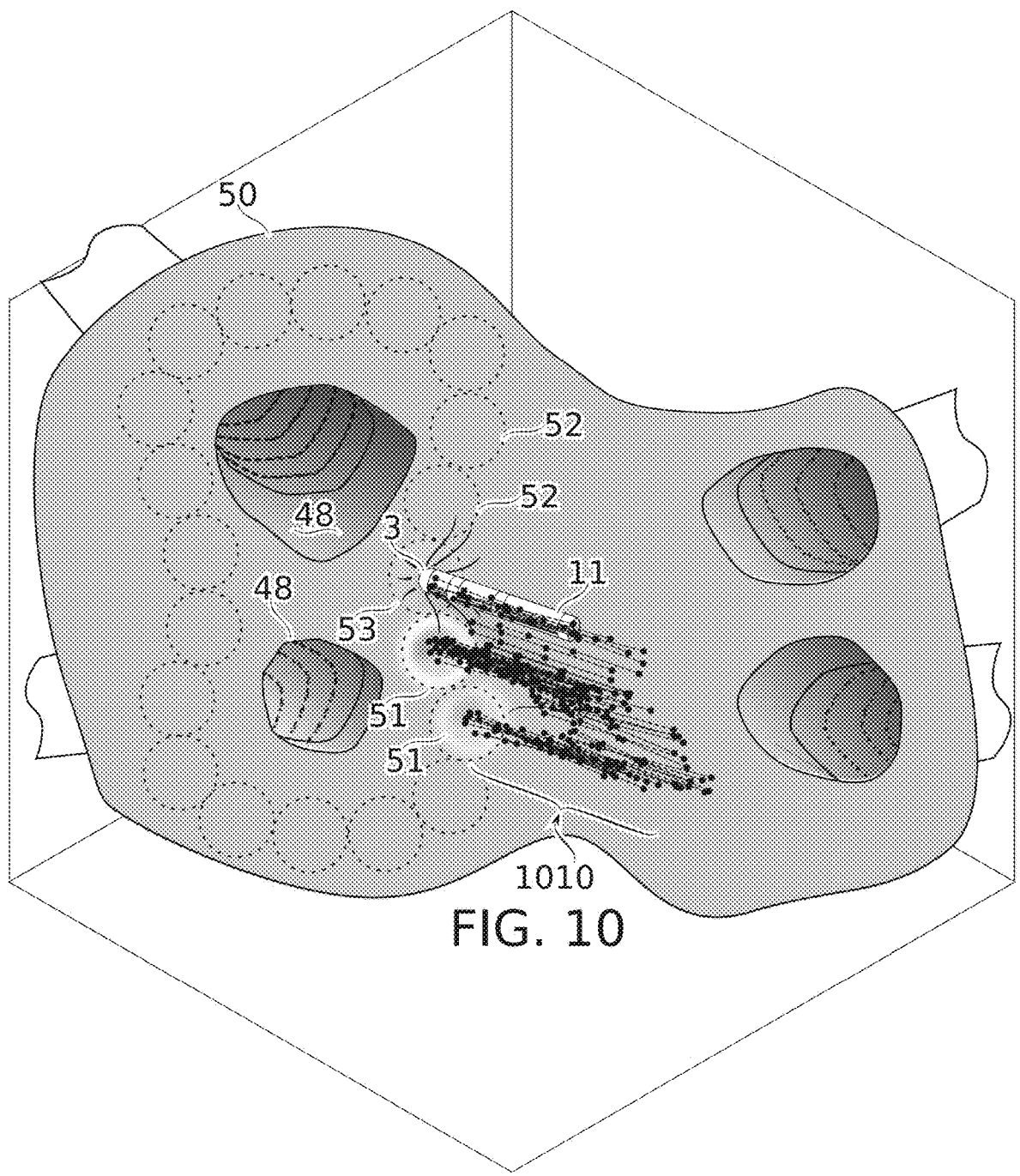
FIG. 10 schematically represents refinement and use of a reconstructed map of a body cavity during lesioning of body cavity tissue, according to some exemplary embodiments of the present disclosure.

Reference is now made to FIG. 10, which schematically represents refinement and use of a reconstructed map of a body cavity during lesioning of body cavity tissue, according to some exemplary embodiments of the present disclosure.

In some embodiments, a goal of ablation procedures to treat atrial fibrillation, is to electrically isolate regions of cardiovascular tissue involved in triggering fibrillation episodes from the main body of the heart. In some embodiments, the plan for achieving this goal comprises forming an ablation line in the heart wall comprising a chained-together sequence of smaller lesions. In FIG. 10, circles 52 indicate planned positions for lesions in a left atrial wall tissue 50, in order to isolate electrogenic sources in one or more pulmonary veins 48. Two already placed lesions 51 are shown, as well as a partial lesion 53 in the process of ablation. The relative positioning of placed lesions 51 following the ablation plan can have a significant impact on the prognosis for success, since gaps between the smaller lesions 51 can allow electrical reconnection, and failure of the treatment as a possible result.

In some embodiments of the invention, continual updating of a body cavity reconstruction based on voltage measurement readings from the ablation probe 11 itself as it moves around the heart helps to increase the resolution, precision, and/or accuracy of the body cavity reconstruction at the places where the activity (and, potentially, interest and/or importance to the procedure) is also increased. Moreover, insofar as correct relative placement of the small lesions is a significant factor in procedure success, it is a potential advantage to include recent, nearby position data in the reconstruction which is used to guide subsequent positioning. For example, in some embodiments, locations of already made lesions may be marked on a view of the reconstruction model, e.g., as colored circles of a size indicative of the lesion size. Cloud 1010 represents just the locations, to which the most recent voltage measurements have been transformed during the ongoing formation of an ablation line. The sampling density shown is reduced for purposes of illustration. Voltage measurements are optionally taken at a relatively high frequency compared to the size and motions of the probe, so the spatial sampling interval during careful positioning movements is usually less than about 10% of the probe diameter. For example, a sampling rate of about 100 measurements per second while moving a 1 mm diameter probe about 10 mm per second would result in a measurement every 100 µm). As a result, there will usually be a substantial number of neighboring-position voltage measurements available for use in determining a current ablation probe position in relation to recent ablations.

The creation of small lesions typically requires several seconds of fixed positioning of an ablation probe, so that there is also ample time to acquire phasic information, for example as described in relation to FIGS. 5A-5E. This phasic information can be used in different ways to assist positioning during a procedure, as is now described.

In some embodiments of the current invention, there is a tradeoff, when displaying an intrabody probe position within a heart chamber reconstruction model, between showing phasic motions of the heart and/or probe ("phasic fidelity" in the discussion that follows), and suppressing those motions ("phasic stabilization"). Optionally, actual phasic motions are displayed (insofar as available information allows), with full phasic fidelity, full phasic stability, or some intermediate combination of the two.

Greater phasic fidelity has the potential advantage of making it clearer to an operator what control motions of the intrabody probe (e.g., catheter manipulations) are actually possible, and what their effects are likely to be. For example, as a probe approaches a heart wall, it can intermittently fall in and out of contact with beating tissue. Seeing this clearly represented can help to guide an operator to determine whether more advance is needed to reach the tissue wall before beginning a treatment. Displaying with greater phasic stabilization, on the other hand, has the potential advantage of removing distracting motions from the view of the operator, to facilitate concentration on identifying and reaching a target position.

In some embodiments of the invention, stabilization of/fidelity to phasic motions is divided according to different types of phasic motion. Phasic motion which identically affects both an intrabody probe and the cavity in which it is positioned (e.g., a rigid translation component of phasic motion) will often be of little interest to an operator, since the relative positions of the two remain unchanged by such motion. In some embodiments, this component is preferably suppressed for the operator (e.g., the motion is not reproduced on a view provided to the operator that shows a position of the probe within a reconstruction).

In many situations, beating of a heart results in repeated expansions and contractions that change the relative position of heart wall and intrabody probe. In some embodiments, the heart wall is shown in a substantially fixed position (at least, within the duration of one heartbeat), and the probe is shown to move. Display of this kind of relative motion would be a typical result if phasic changes in electromagnetic field and/or cavity geometry were not specifically accounted for. However, the resulting apparent motion is not only potentially rather artificial-seeming, but it can also be distracting to an operator trying to reach a specific target.

In some embodiments, an optional display mode having greater phasic fidelity represents relative motions due tissue movement as displayed tissue movement, while the probe itself remains relatively stationary in the display. This motion is optionally approximated based in partial data, and does not need to be rendered with best available accuracy to be useful. For example, the whole heart is optionally moved according to a stereotyped phasic pattern with only a small number of parameters being determined from current measurements. This approach could be used to maintain an accurate representation of distance between the tip of an intrabody probe and the tissue it is nearest to, while other phasic movements are represented as suggestive of actual ongoing motion, without necessarily being as accurate.

In some embodiments of the invention, phasic relative probe/tissue motion is optionally divided into both a component due to phasic motion of the tissue, and a component due to phasic motion of the probe because it is disturbed by motion of the tissue. Optionally, separating of these motions is performed (statistically, for example) by comparing changes in the measured environment of the probe 11 when in contact and when not in contact with the tissue wall, for a particular region. Measured out-of-contact motion not accounted for by measured in-contact motion is optionally assigned to be "probe motion". Additionally or alternatively, phasic motions of the probe as such are accounted for based on physical analysis of the motion of anchoring anatomy of the intrabody probe 11 (e.g., movements of fossae and/or vascular roots by which a probe 11 enters a heart). Optionally, such analysis taking into account the extent by which a distal end of the intrabody probe has passed such an anchoring region.

In some embodiments, display of both phasic tissue motion and phasic probe motion are suppressed (phasic stabilization), insofar as some metric of relative position can also be stabilized. For example, displayed distances between a probe 11 and heart wall tissue 50 are optionally displayed relative to some particular phase of the heartbeat cycle. Optionally, for example, when the actual probe position extends past the displayed position of the tissue wall it is near, the displayed probe position is nevertheless maintained at the position of the wall. Optionally, there is some other displayed indication of increased advance of the probe toward the wall, such as distortion of the contacted wall region as if it is experiencing increased force of contact.

Phasic stabilization and phasic fidelity are optionally intermingled, in some embodiments. For example, display of phasic motion of body tissue is substantially suppressed in some embodiments as just described (e.g., walls of a heart chamber are displayed not beating). However, where probe 11 experiences intermittent contacts and/or forces due to phasic motion, a constant or a phase-varying indication (e.g., distortion of tissue or probe) at a region of tissue contact is optionally displayed to indicate this. This indication does not necessarily indicate the phasic motion over the whole displayed representation of the structure undergoing phasic motion.

It should also be noted that phasic intra-beat changes in heart size due to heart beat are optionally treated distinctly from beat-to-beat changes in displayed heart size due to changes in heart rate, for example as described herein in relation to FIGS. 5A-5D.

Inputs and Functions of a Reconstruction Service Module

Figure 11:
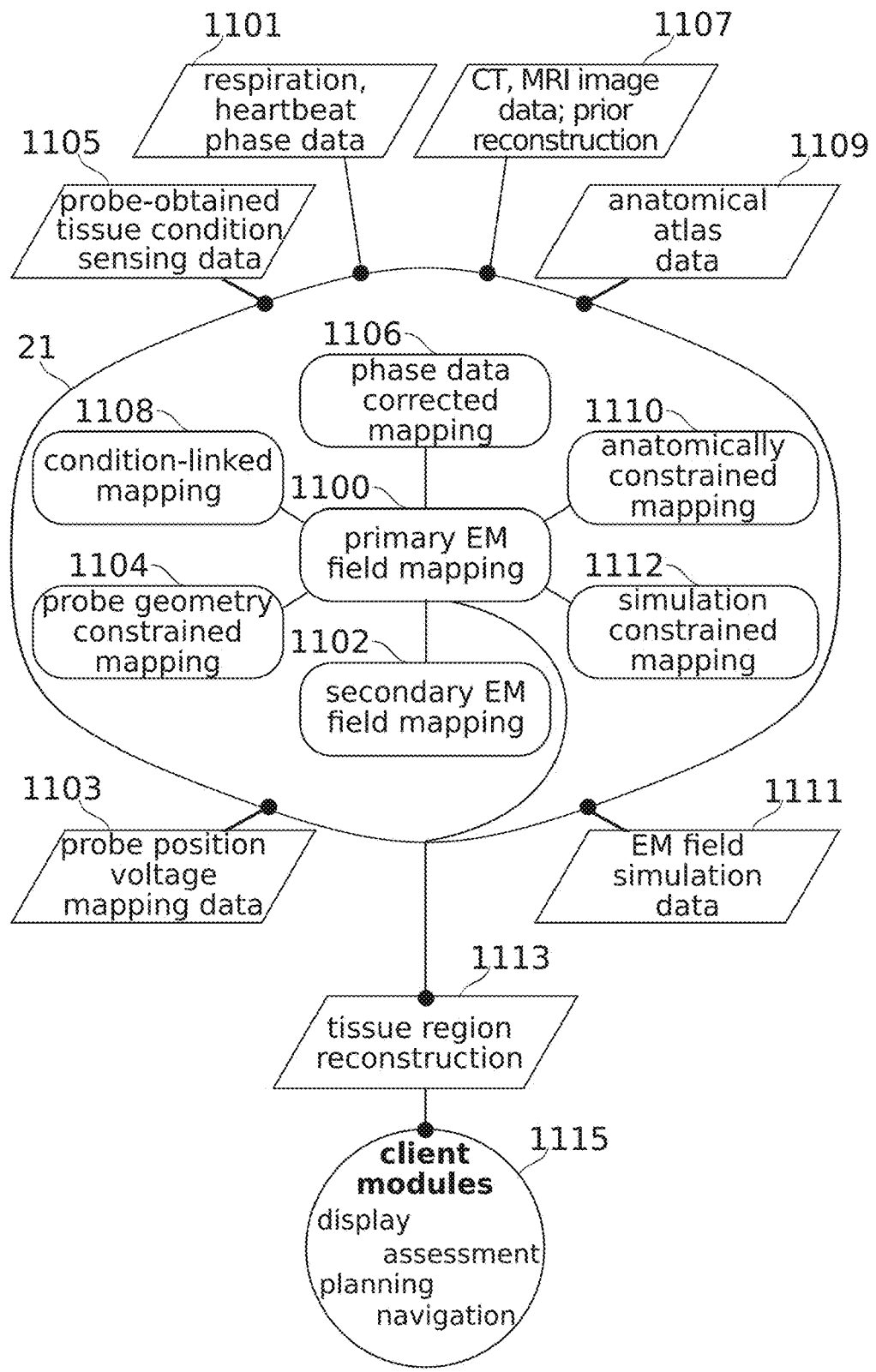
FIG. 11 schematically represents inputs to and functions performed by a reconstruction service module, according to some exemplary embodiments of the present disclosure.

Reference is now made to FIG. 11, which schematically represents inputs to and functions performed by a reconstruction service module 21, according to some exemplary embodiments of the present disclosure.

FIG. 11 collects together functions of reconstruction service module 21 provided in some embodiments of the current invention, and described in relation to the other figures herein, for example as indicated below. Not all functions are provided in every embodiment of the current invention; rather they are optionally provided in any suitable combination of available input and reconstruction-supporting functions described herein. In some embodiments, reconstruction service module 21 is implemented as computer code, optionally in conjunction with digital signal processing (DSP) and/or graphical processing hardware specialized for signal and/or image processing. Implementation is optionally within a single computing device, or distributed among a plurality of computing devices. Each of the functionality blocks 1102, 1104, 1106, 1108, 1110, and 1112 shown within reconstruction service module 21 represents a different contribution to primary (i.e., "overall") EM mapping functionality 1100. Any of these functionality blocks is optionally provided by reconstruction service module 21. Each of functionality blocks 1102, 1104, 1106, 1108, 1110, and 1112 may be understood as contributing to the primary EM field mapping functionality 1100 according to their own specific capabilities. Optionally, contribution to mapping is by any suitable combination of the operations of functionality blocks 1102, 1104, 1106, 1108, 1110, and 1112.

Basic input for reconstruction, in some embodiments, comprises probe position voltage mapping data 1103, which may include, for example, data indicative of voltage measurements made by various electrodes on the probe, where each measurement is associated with an identifier of the electrode that made the measurement, and the frequency at which the measurement was made. The probe position voltage mapping data 1103 optionally are provided with respect to at least three crossed electromagnetic fields, and optionally with respect to any number of electromagnetic fields (for example, as described in relation to FIGS. 8A-8B and 9A-9B).

In some embodiments, and using position voltage mapping data 1103, the probe geometry constrained mapping functionality block 1104 produces a voltage/spatial mapping, for example as detailed in relation to block 112 of FIG. 1A. Optionally, this is performed in conjunction with one or more spatial coherence criteria. In some embodiments, this voltage/spatial mapping serves as a base mapping which the other functionality blocks 1102, 1106, 1108, 1110, and 1112 optionally act upon and modify (as further explained herein below).

As output, reconstruction service module 21 produces a tissue region reconstruction 1113. Reconstruction 1113 in turn is optionally used by one or more client modules 1115. Use of the tissue region reconstruction is detailed, for example, in relation to block 114 of FIG. 1A. Client modules 1115 can be any hardware or software implementation of functionality described in relation to block 114, such as the functionality of display and/or navigation, procedure assessment, procedure planning and/or replanning, or another functionality.

Modifications produced by the remaining functionality blocks 1102, 1106, 1108, 1110, and 1112 are now described in turn.

Optionally, where more than three (for example) primary electromagnetic fields are used in generating probe position voltage mapping data 1103, reconstruction service module 21 implements electromagnetic field mapping 1102, using "extra" fields. These can be electrical fields generated using body surface electrodes, for example as described in relation to FIGS. 8A-8B and 9A-9B; using electrodes on other intrabody probes besides that used to sense probe position voltage mapping data 1103; and/or using electrodes on the same probe used for sensing.

Optional first auxiliary inputs 1107 used in some embodiments of the invention may include CT, and/or MRI image data and/or reconstruction data (such as probe position voltage mapping data) obtained from the patient during an earlier procedure, or earlier in the present procedure. Additionally or alternatively, a second set of auxiliary input may include anatomical atlas data 1109. Auxiliary inputs 1107 and 1109 correspond, in some embodiments, to the anatomical data 31 of FIG. 12. Optionally, these auxiliary inputs are used by functions of anatomically constrained mapping functionality block 1110 in reconstruction service module 21. The anatomically constrained mapping functionality block 1110 optionally uses one or more of the auxiliary data inputs 1107, 1109 to help scale and/or orient the tissue region reconstruction 1113. Optionally, one or more of auxiliary inputs 1107, 1109 is used to help identify position sensing errors—for example, a sensed position located in a place that is determined to be not physically accessible may be disregarded in producing tissue region reconstruction 1113.

Optionally, electromagnetic field simulation data 1111 are provided (corresponding, in some embodiments, to electromagnetic field simulation data 32) for use by functions of simulation constrained mapping 1112 in reconstruction service module 21. The electromagnetic field simulation data 1111 is optionally based in turn on one or both of auxiliary input data 1107, and/or 1109. Electromagnetic field simulation is described, for example, in relation to FIG. 7 herein.

Optionally, tissue region reconstruction 1113 includes correction for phases of heartbeat and/or respiration, based on respiration and/or heartbeat data 1101 according to processing by functionality of reconstruction service module 21 for phase data corrected mapping 1106. This is described, for example, in relation to FIGS. 3A-3C and 5A-5E herein.

Optionally, tissue region reconstruction 1113 is generated and/or refined based on probe-measured tissue condition sensing data 1105, as processed, for example, by functionalities of reconstruction service module 21 for condition-linked mapping 1108. This is described, for example, in relation to FIG. 6, herein.

General

It is expected that during the life of a patent maturing from this application many relevant intrabody probes will be developed; the scope of the term intrabody probe is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of reconstructing a body cavity shape of a subject based on intrabody measurements of a plurality of crossing electromagnetic fields established within the body cavity, the method comprising:

receiving measurements of the plurality of crossing electromagnetic fields, wherein the measurements collectively define a cloud of measurements in a measurement space, and are measured using two sensors carried on an intrabody probe at a known distance from each other, the measuring being carried out with the intrabody probe at multiple locations in the body cavity; and reconstructing a shape of the body cavity encoded as spatial position data in a computer memory, and in a format encoding sufficient detail to guide computerized generation of an image of the body cavity shape, by transforming the received cloud of measurements;

wherein the reconstructing comprises assigning the measurements of the plurality of crossing electromagnetic fields to locations selected to reduce cost of a cost function, the cost function being increased as a function both of:

distances between sister locations becoming increasingly different than the known distance, and nearby measurements becoming increasingly different;

wherein the cost of increasing difference between nearby measurements itself increases as a function of decreasing distance between respective assigned locations of said nearby measurements;

wherein sister locations are locations assigned to sister measurements by the reconstructing, and sister measurements are measurements of the plurality of crossing electromagnetic fields measured substantially simultaneously by the two sensors carried on the intrabody probe at the known distance from each other.

2. The method of claim 1, wherein reduction of variability in distances between sister locations comprises reducing differences between distances of sister locations and the known distance.

3. The method of claim 1, wherein the reconstructing comprises assigning the measurements of the plurality of crossing electromagnetic fields to locations in a segmentation preserving manner.

4. The method of claim 1, wherein the reconstructing comprises assigning the measurements of the plurality of crossing electromagnetic fields to locations by a measurement-to-location transform decomposable to components of different spatial frequencies, and minimizing high frequency components of the transform.

5. The method of claim 1, wherein the measurements of the plurality of crossing magnetic fields are taken by three or more sensors.

6. The method of claim 5, wherein at least the distance between two of the three or more sensors is unknown.

7. The method of claim 1, wherein the intrabody probe sensors comprise electrodes.

8. The method of claim 7, wherein the sensors measure voltage.

9. The method of claim 8, wherein the voltage indicates impedance.

10. The method of claim 1, wherein the measurements of the plurality of crossing magnetic fields include voltage measurements.

11. The method of claim 1, wherein the measurements of the plurality of crossing electromagnetic fields include impedance measurements.

12. The method of claim 1, wherein the intrabody probe comprises more than two sensors fixed to a rigid portion of the intrabody probe, each sensor being at a known distance from at least one other sensor, and together with each such at least one other sensor defines a respective pair of sensors from which measurements related as sister measurements are measured, said measurements related as sister measurements also being assigned to sister locations by the reconstructing, and wherein the cost function also increases as distances between the sister locations defined from said measurements related as sister measurements are increasingly different than their respective known distance.

13. The method of claim 1, wherein the plurality of crossing electromagnetic fields comprise at least one electromagnetic field established between electrodes of the sensors.

14. The method of claim 1, comprising:

receiving data indicative of measurements of at least one parameter varying in time together with a change in the body cavity shape;

wherein reconstructing comprises using the data indicative of the at least one parameter to reduce an effect of the change in the body cavity shape on the reconstruction.

15. The method of claim 14, wherein the at least one parameter varying in time comprises a heartbeat phase of the subject.

16. The method claim 14, wherein the at least one parameter varying in time comprises a respiratory phase of the subject.

17. The method of claim 14, wherein reconstructing comprises minimizing a volume in physical space to which static measurements are transformed, wherein the static measurements are measurements measured when the intrabody probe is immobilized against a moving tissue of the body cavity.

18. The method of claim 1, comprising repeating the reconstructing as new measurements become available and are received, the reconstructing being repeated at a rate of at least 1 Hz.

19. The method of claim 18, comprising repeatedly generating the image of the body cavity shape as the reconstructing is repeated, including an indication displaying an indication in the image corresponding to a position of the intrabody probe while at least one of the new measurements was made.

20. The method of claim 19, comprising repeatedly displaying the images of the body cavity shape as the image of the body cavity shape is regenerated.

21. The method of claim 1, comprising generating the image of the body cavity shape.

22. The method of claim 1, wherein the cloud of measurements comprises at least 604 measurements.

23. An apparatus for reconstructing a body cavity shape of a subject based on intrabody measurements of a plurality of crossing electromagnetic fields established within the body cavity, the apparatus comprising:

computer circuitry, configured to receive measurements of the plurality of crossing electromagnetic fields, wherein the measurements collectively define a cloud of measurements in a measurement space, and are measured using two sensors carried on an intrabody probe at a known distance from each other, the measuring being carried out with the probe at multiple locations in the body cavity, and reconstruct a shape of the body cavity encoded as spatial position data in a computer memory, and in a format encoding sufficient detail to guide computerized generation of an image of the body cavity shape, by transforming the received cloud of measurements by assigning the measurements of the plurality of crossing electromagnetic fields to locations selected to reduce cost of a cost function, the cost function being increased by both of:

distances between sister locations increasingly different than the known distance, and increased differences in the measurements associated with increasing closeness of their assigned locations;

wherein sister locations are locations assigned to sister measurements, and sister measurements are measurements of the plurality of crossing electromagnetic fields measured substantially simultaneously by the two sensors carried on the intrabody probe at the known distance from each other.

24. The apparatus of claim 23, wherein the computer circuitry is configured to assign the measurements of the plurality of crossing magnetic fields to locations in a segmentation preserving manner.

25. The apparatus of claim 23, wherein the computer circuitry is configured to assign the measurements of the plurality of crossing magnetic fields to locations by a measurement-to-location transform decomposable to components of different spatial frequencies, and minimizing high frequency components of the transform.

26. The apparatus of claim 23, provided together with the intrabody probe.

27. The apparatus of claim 26, wherein the intrabody probe comprises three or more sensors.

28. The apparatus of claim 27, wherein at least a distance between two of the three or more sensors is unknown.

29. The apparatus of claim 26, wherein the sensors of the intrabody probe comprise electrodes.

30. The apparatus of claim 26, wherein the sensors measure voltage.

31. The apparatus of claim 23, wherein the plurality of crossing electromagnetic fields comprise at least one electromagnetic field established between electrodes of the sensors.

32. The apparatus of claim 23, wherein the computer circuitry is configured to receive data indicative of measurements of at least one parameter varying in time together with a change in the body cavity shape; and use the data indicative of the at least one parameter to reduce an effect of the change in the body cavity shape on the reconstruction.

33. The apparatus of claim 32, wherein the computer circuitry is configured to minimize a volume in physical space, to which static measurements are transformed, wherein the static measurements are measurements measured when the intrabody probe is immobilized against a moving tissue of the body cavity.

* * * * *